(12) United States Patent
Verdin et al.

(10) Patent No.: US 8,114,853 B2
(45) Date of Patent: Feb. 14, 2012

(54) METHODS OF TREATING SMOOTH MUSCLE CELL DISORDERS

(75) Inventors: Eric M. Verdin, San Francisco, CA (US); David Waltregny, Liege (BE); Vincent Castronovo, Liege (BE)

(73) Assignee: The J. David Gladstone Institutes, San Francisco, CA (US)

( * ) Notice: Subject to any disclaimer, the term of this patent is extended or adjusted under 35 U.S.C. 154(b) by 341 days.

(21) Appl. No.: 12/567,500

(22) Filed: Sep. 25, 2009

(65) Prior Publication Data

US 2010/0022624 A1 Jan. 28, 2010

Related U.S. Application Data

(62) Division of application No. 11/166,669, filed on Jun. 23, 2005, now abandoned.

(60) Provisional application No. 60/583,267, filed on Jun. 25, 2004.

(51) Int. Cl.
*A61K 31/70* (2006.01)
*C12Q 1/68* (2006.01)
*C07H 21/02* (2006.01)
*C07H 21/04* (2006.01)
*C12N 5/00* (2006.01)

(52) U.S. Cl. ............ 514/44 A; 514/1; 514/2; 424/130.1; 435/375; 435/377

(58) Field of Classification Search .................. None
See application file for complete search history.

(56) References Cited

U.S. PATENT DOCUMENTS

| 7,288,567 B2 | 10/2007 | Delorme et al. |
| 2004/0259247 A1 | 12/2004 | Tuschl et al. |
| 2007/0031844 A1 | 2/2007 | Khvorova et al. |

FOREIGN PATENT DOCUMENTS

WO WO 0142437 6/2001

OTHER PUBLICATIONS

Durst et al. The inv(16) fusion protein associates with corepressors via a smooth muscle myosin heavy-chain domain. (2003) Mol. Cell Biol. 23: 607-619.
Li et al. Proceedings of the American Association for Cancer Research, 2003, vol. 44, pp. 343.
Waltregny et al., Histone deacetylase HDAC8 associates with smooth muscle alpha-actin and is essential for smooth muscle cell motility. The FASEB Journal, Mar. 16, 2005, pp. 1-24.
Waltregny, Expression of histone deacetylase 8, a class I histone deacetylase, is restricted to cells showing smooth muscle differentiation in normal human tissue. American Journal of Pathology, vol. 165, No. 2, pp. 553-564.
Wedel, Novel smooth muscle markers reveal abnormalities of intestinal musculature in severe colorectal motility disorders. Neurogastroenterol. Motil. vol. 18, pp. 526-538.
Waltregny, Screening of histone decetylases (HDAC) expression in human prostate cancer reveals distinct class I HDAC profiles between epithelial and stromal cells. vol. 48, No. 3, pp. 273-290.

*Primary Examiner* — Sean McGarry
(74) *Attorney, Agent, or Firm* — Paula A. Borden; Bozicevic Field & Francis LLP

(57) ABSTRACT

The present invention provides methods of detecting cells showing smooth muscle differentiation. The present invention further provides methods of detecting tumor cells. The present invention further provides compositions and methods for treating smooth muscle cell disorders.

13 Claims, 10 Drawing Sheets

SEQUENCE LISTING

<160> NUMBER OF SEQ ID NOS: 41

<210> SEQ ID NO 1
<211> LENGTH: 1743
<212> TYPE: DNA
<213> ORGANISM: H. sapiens

<400> SEQUENCE: 1
gccagatctg gaaggtggct gcggaacggt tttaagcgga agatggagga gccggaggaa    60

```
ccggcggaca gtgggcagtc gctggtcccg gtttatatct atagtcccga gtatgtcagt    120
atgtgtgact ccctggccaa gatccccaaa cgggccagta tggtgcattc tttgattgaa    180
gcatatgcac tgcataagca gatgaggata gttaagccta aagtggcctc catggaggag    240
atggccacct tccacactga tgcttatctg cagcatctcc agaaggtcag ccaagagggc    300
gatgatgatc atccggactc catagaatat gggctaggtt atgactgccc agccactgaa    360
gggatatttg actatgcagc agctatagga ggggctacga tcacagctgc caatgcctg    420 attgacggaa tgtgcaaagt agcaattaac tggtctggag ggtggcatca tgcaaagaaa    480
gatgaagcat ctggtttttg ttatctcaat gatgctgtcc tgggaatatt acgattgcga    540
cggaaatttg agcgtattct ctacgtggat ttggatctgc accatggaga tggtgtagaa    600
gacgcattca gtttcacctc caaagtcatg accgtgtccc tgcacaaatt ctccccagga    660
tttttcccag aacaggtga cgtgtctgat gttggcctag gaagggacg gtactacagt     720 gtaaatgtgc ccattcagga tggcatacaa gatgaaaaat attaccagat ctgtgaaagt    780
gtactaaagg aagtatacca agcctttaat cccaaagcag tggtcttaca gctgggagct    840
gacacaatag ctggggatcc catgtgctcc tttaacatga ctccagtggg aattggcaag    900
tgtcttaagt acatccttca atggcagttg gcaacactca ttttgggagg aggaggctat    960
aaccttgcca cacggctcg atgctggaca tacttgaccg gggtcatcct agggaaaaca   1020
ctatcctctg agatcccaga tcatgagttt ttcacagcat atggtcctga ttatgtgctg   1080
gaaatcacgc caagctgccg gccagaccgc aatgagcccc accgaatcca acaaatcctc   1140
aactacatca agggaatctc gaagcatgtg gtctagttga cagaaagaga tcaggtttcc   1200
agagctgagg agtggtgcct ataatgaaga cagcgtgttt atgcaagcag tttgtggaat   1260
ttgtgactgc agggaaaatt tgaaagaaat tacttcctga aaatttccaa ggggcatcaa   1320
gtggcagctg gcttcctggg gtgaagaggc aggcacccca gagtcctcaa ctggacctag   1380
gggaagaagg agatatccca catttaaagt tcttatttaa aaaacacac acacacaaat   1440 gaaatttta atctttgaaa attatttta agcgaattgg ggaggggagt attttaatca     1500
tcttaaatga aacagatcag aagctggatg agagcagtca ccagtttgta gggcaggagg   1560
cagctgagag gcagggtttg ggcctcagga ccatccaggt ggagccctgg gagagagggt   1620
actgatcagc agactgggag gtggggagaa gtccgctggt gttgttttag tgttatatat   1680
ctttggtttt tttaataaaa tctttgaaaa cctaaaaaaa aaaaaaaaaa aaaaaaaaa    1740 aaa                                                                 1743

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
caccatggag gagccggagg aa                                              22

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
```

```
gaccacatgc ttcagattcc ctt                                              23

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
atggaggagc cggaggaacc gg                                               22

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
acatgcttca gattcccttt gat                                              23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gaggagccgg aggaaccggc gg                                               22

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gcttcagatt ccctttgatg tag                                              23

<210> SEQ ID NO 8
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with t's
      at positions 20 and 21

<400> SEQUENCE: 8
ugagccccac cgaauccaan n                                                21

<210> SEQ ID NO 9
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with t's
      at positions 20 and 21

<400> SEQUENCE: 9
uuggauucgg uggggcucan n                                                21
```

<210> SEQ ID NO 10
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with t's
      at positions 20 and 21

<400> SEQUENCE: 10
acgggccagu auggugcaun n                                              21

<210> SEQ ID NO 11
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with t's
      at positions 20 and 21

<400> SEQUENCE: 11
augcaccaua cuggcccgun n                                              21

<210> SEQ ID NO 12
<211> LENGTH: 39
<212> TYPE: DNA
<213> ORGANISM: Artificial Sequence
<220> FEATURE:
<221> NAME/KEY:
<222> LOCATION:
<223> OTHER INFORMATION: synthetic sequence

<400> SEQUENCE: 12
tgagccccac cgaatccaan ttggattcgg tggggctca                           39

<210> SEQ ID NO 13
<211> LENGTH: 47
<212> TYPE: DNA
<213> ORGANISM: Artificial Sequence
<220> FEATURE:
<221> NAME/KEY:
<222> LOCATION:
<223> OTHER INFORMATION: synthetic sequence

<400> SEQUENCE: 13
tgagccccac cgaatccaat ttttgcttgg attcggtggg gctcatt                  47

<210> SEQ ID NO 14
<211> LENGTH: 39
<212> TYPE: DNA
<213> ORGANISM: Artificial Sequence
<220> FEATURE:
<221> NAME/KEY:
<222> LOCATION:
<223> OTHER INFORMATION: synthetic sequence

<400> SEQUENCE: 14
acgggccagt atggtgcatn atgcaccata ctggcccgt                           39

<210> SEQ ID NO 15
<211> LENGTH: 43
<212> TYPE: DNA
<213> ORGANISM: Artificial Sequence
<220> FEATURE:
<221> NAME/KEY:

```
<222> LOCATION:
<223> OTHER INFORMATION: synthetic sequence

<400> SEQUENCE: 15
acgggccagt atggtgcatt ttgcatgcac catactggcc cgt                          43

<210> SEQ ID NO 16
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with
      t's at positions 20 and 21

<400> SEQUENCE: 16
cugcaaggga uggaucugan n                                                  21

<210> SEQ ID NO 17
<211> LENGTH: 21
<212> TYPE: DNA
<213> ORGANISM: Artificial Sequence
<220> FEATURE:
<221> NAME/KEY:
<222> LOCATION:
<223> OTHER INFORMATION: synthetic sequence; RNA construct with t's
      at positions 20 and 21

<400> SEQUENCE: 17
ucagauccau cccuugcagn n                                                  21

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
accgggcaac gttacgaat                                                     19

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ctatcaaagg acacgccaag tg                                                 22

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
caccgcctcc cagcatcagc a                                                  21

<210> SEQ ID NO 21
<211> LENGTH: 24
<212> TYPE: DNA
<213> ORGANISM: Artificial Sequence
<220> FEATURE:
<223> OTHER INFORMATION: primer
```

<400> SEQUENCE: 21
tcattggaaa attgacagca tagt                                    24

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
catggtgatg gtgttgaaga ag                                      22

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
ccttttccag caccaatatc cctcaagt                                28

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ttgagttctg ctcgcgttac a                                       21

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cccagttaat ggcaatatca cagat                                   25

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
ctctgcaagg agcaacccag ctgaa                                   25

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
aatctgaacc actgcatttc ca                                      22

<210> SEQ ID NO 28
<211> LENGTH: 23

```
<212> TYPE: DNA
<213> ORGANISM: Artificial Sequence
<220> FEATURE:
<223> OTHER INFORMATION: primer

<400> SEQUENCE: 28
ggtggttata ggaggtcgac act                                              23

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
aacgcagcac agttcccttg accag                                            25

<210> SEQ ID NO 30
<211> LENGTH: 24
<212> TYPE: DNA
<213> ORGANISM: Artificial Sequence
<220> FEATURE:
<223> OTHER INFORMATION: primer

<400> SEQUENCE: 30
ttggagacgt ggagtacctt acag                                             24

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
gactaggacc acatcaggtg agaac                                            25

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tggtgatgcc cattgcccac g                                                21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
tggctattgc atgttcaacc a                                                21

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
gtcgaaggtg aactgtgttc ct                                               22
```

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
cccgctatgc tcaacagaaa caccg                                     25

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
ctgcattgga ggaatgaagc t                                         21

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
ctggcacagc ggatgtttg                                            19

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
tgtcagtgtc caccccaacc cca                                       23

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
tcccgagtat gtcagtatat atga                                      24

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
gcttcaatca aagaatgcac cat                                       23

<210> SEQ ID NO 41
<211> LENGTH: 22
<212> TYPE: DNA
<213> ORGANISM: Artificial Sequence
<220> FEATURE:
<223> OTHER INFORMATION: primer

```
<400> SEQUENCE: 41
cctggccaag atccccaaac gg                                            22
```

METHODS OF TREATING SMOOTH MUSCLE CELL DISORDERS

CROSS-REFERENCE

This application is a divisional of U.S. patent application Ser. No. 11/166,669, filed on Jun. 23, 2005, and claims the benefit of U.S. Provisional Patent Application No. 60/583,267, filed Jun. 25, 2004, which applications are incorporated herein by reference in their entirety.

FIELD OF THE INVENTION

The present invention is in the field of smooth muscle differentiation, and in particular methods of treating smooth muscle cell disorders, and methods of identifying cells showing smooth muscle differentiation.

BACKGROUND OF THE INVENTION

Modification of chromatin structure via the reversible acetylation of nucleosomal histones plays an important role in the regulation of transcription in eukaryotic cells. Acetylation of the C-amino group of specific lysine residues within the amino terminal tail of core histones results in localized chromatin relaxation. This acetylation is required to maintain the unfolded structure of nucleosomes undergoing transcription. In general, histone acetylation activity correlates with transcriptional activation, whereas deacetylation activity correlates with transcriptional repression. The regulation of histone acetylation levels in vivo is a dynamic process under the control of competing enzymes within the nucleus of a cell: histone acetyltransferases (HATs) and histone deacetylases (HDACs).

Currently, over a dozen HATs have been identified and at least 18 different members of the HDAC family have been isolated from mammalian cells. The first cDNA encoding HDAC to be cloned was the yeast protein Rpd3, which was identified in genetic screens for transcriptional repressors. Mammalian HDAC1 was cloned independently as the molecular target of trichostatin A (TSA), a fungal toxin. HDAC1 was observed to be an ortholog of yeast Rpd3, and both were shown to have HDAC activity in vitro.

HDACs are usually separated into 3 classes on the basis of their similarity to various yeast histone deacetylases: (i) class I members, including HDAC1, HDAC2, HDAC3, HDAC8, and HDAC11, which are homologous to the yeast Rpd3 protein 5-11 (ii) class II HDACs, including HDAC4, HDAC5, HDAC6, HDAC7, HDAC9, and HDAC10, which have similarities to yeast Hda1 and, (iii) nicotinamide adenine dinucleotide (NAD)-dependent sirtuin (SIRT) proteins, which are homologous to the yeast Sir2 protein. Up to now, 7 human SIRT homologues have been identified.

Class I HDACs have approximately 350-500 amino acids and their transcript expression is considered ubiquitous. Class II HDACs are much larger proteins with around 1000 amino acids; their mRNA distribution is more restricted and they are implicated in the development and differentiation of cardiac and skeletal striated muscle. Class II enzymes can shuttle in and out of the nucleus upon certain cellular signals. Among class I members, HDAC1 and HDAC2 are localized exclusively in the cell nucleus while HDAC3 can be detected in the nuclear and cytoplasm compartments. Database searches for expressed sequence tags showing high similarity with class I HDACs has lead to the cloning of the cDNA for human HDAC8, the fourth identified class I HDAC. This enzyme encodes 377 amino acid residues and is evolutionary most similar to HDAC3 with 34% overall identity.

HDACs mediate transcriptional repression by interacting with larger multisubunit complexes. For example, HDAC1 is known to bind the corepressor Sin3, and HDAC1-Sin3 further associates with the silencing mediators NCoR and SMRT. N-CoR/SMRT-HDAC1 is then recruited by specific transcription factors bound to promoter elements within the nucleus. For example, the retinoblastoma (Rb) gene product recruits N-CoR/SMRT-HDAC1 to bind the transcription factor E2F to repress E2F-regulated promoters. HDAC1-Sin3 also binds to and mediates repression by the MAD/MAX repressor heterodimer. The histone deacetylation activity of HDAC1 is essential for this transcriptional repression.

Recently, it has become clear that a number of non-histone nuclear proteins, such as the tumor suppressor p53, are also substrates for histone deacetylases, which regulate their activity by deacetylation. In addition, some HDACs, such as HDAC6 and SIRT2, are prominently expressed in the cell cytoplasm; these histone deacetylases have been shown to deacetylate a non-histone cytosolic protein: the cytoskeletal protein α-tubulin with concomitant destabilization of dynamic microtubules. Finally, recent reports have suggested a previously unrecognized HDAC location in the cell. Indeed, it has been demonstrated that SIRT3, a human SIR2 homologue, is a mitochondrial NAD-dependent deacetylase, suggesting that this sirtuin may deacetylate a substrate localized in this organelle.

There is a need in the art for methods of treating smooth muscle cell disorders. The present invention addresses this need.

LITERATURE

Durst et al. (2003) *Mol. Cell. Biol.* 23:607-619; WO 01/42437.

SUMMARY OF THE INVENTION

The present invention provides methods of detecting cells showing smooth muscle differentiation. The present invention further provides methods of detecting tumor cells. The present invention further provides compositions and methods for treating smooth muscle cell disorders.

BRIEF DESCRIPTION OF THE DRAWINGS

Figure 7A:
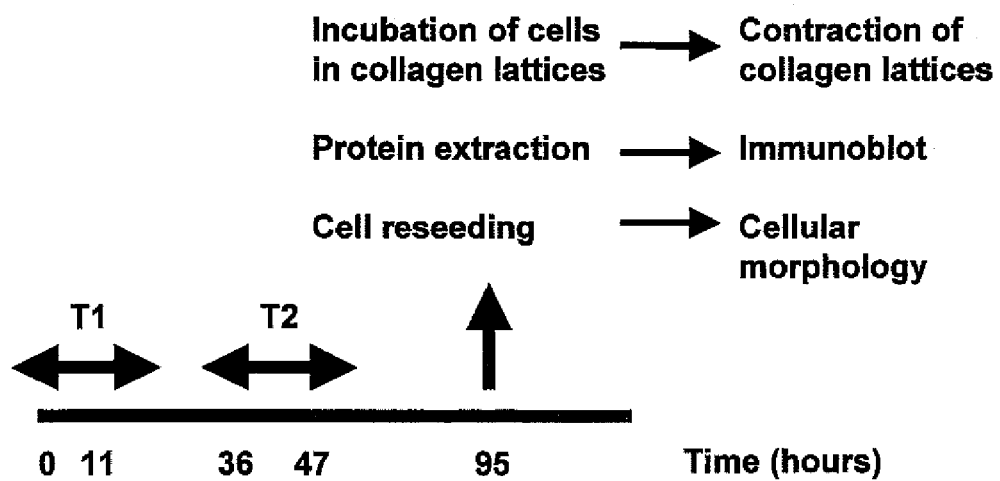
Figure 7B:
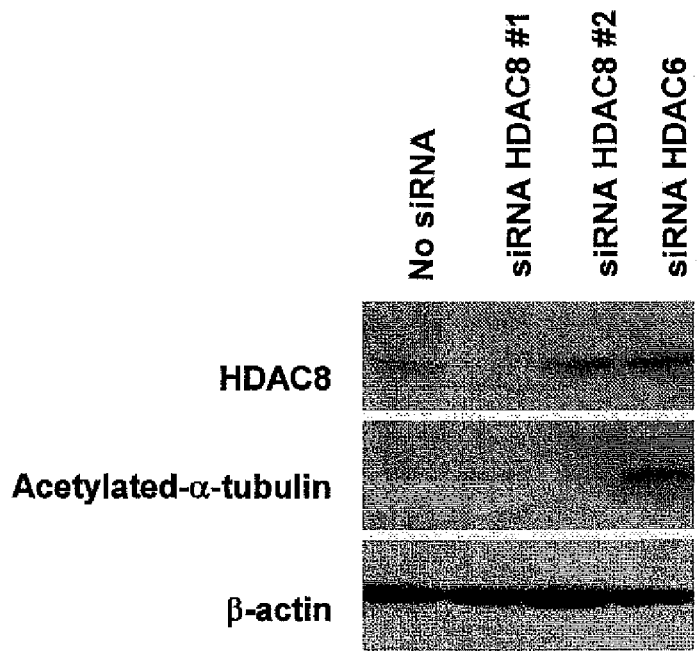

FIGS. 7A and 7B depict a schematic representation of an experimental protocol used to assess the impact of HDAC8 expression silencing by RNA interference on the contraction capability of HSMCs in a collagen contraction assay (FIG. 7A); and reduction of target gene expression with various siRNAs at the start of the collagen interaction assay (FIG. 7B).

Figure 8:
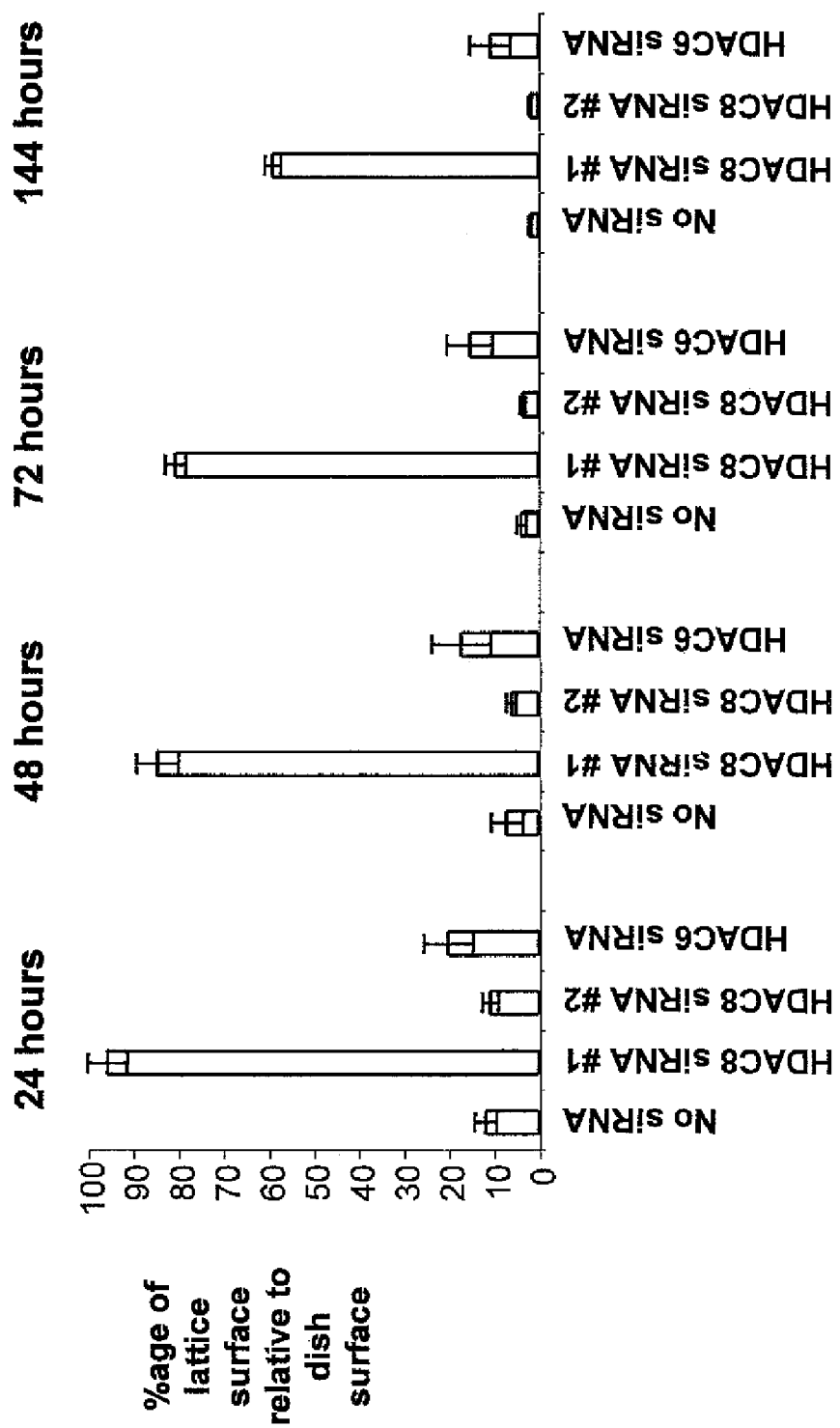

FIG. 8 depicts the effect of HDAC8 siRNA#1 on contraction of collagen lattice.

Figure 9A:
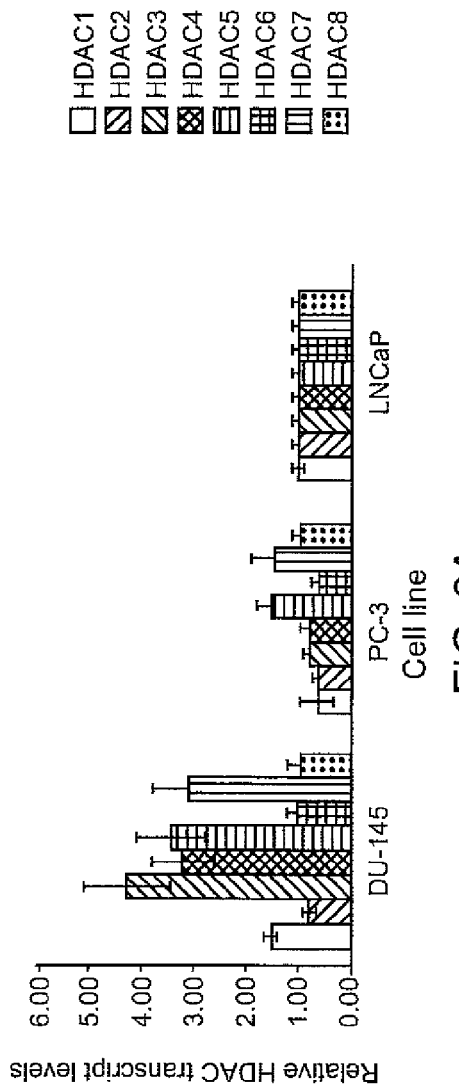
Figure 9B:
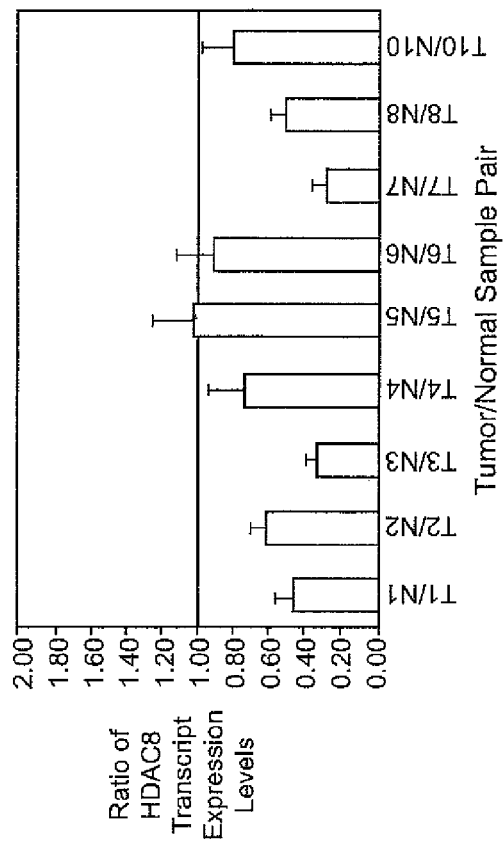

FIGS. 9A and 9B depict analysis of HDAC1, HDAC2, HDAC3, HDAC4, HDAC5, HDAC6, HDAC7, and HDAC8 transcript levels in DU-145, PC-3, and LNCaP cells (FIG. 9A); and the relative level of HDAC8 mRNA in various prostate tumors (FIG. 9B).

Figure 10:
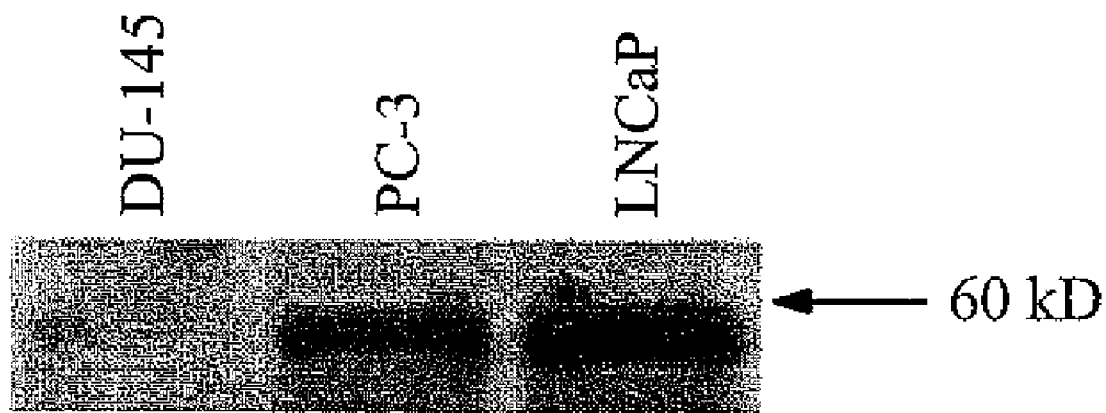

FIG. 10 depicts immunoblot analysis of protein lysates from human DU-145, PC-3, and LNCaP prostate cancer cells.

Figure 11A:
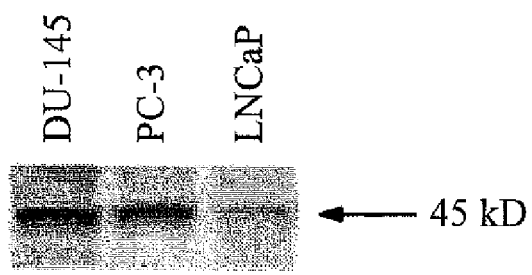
Figure 11B:
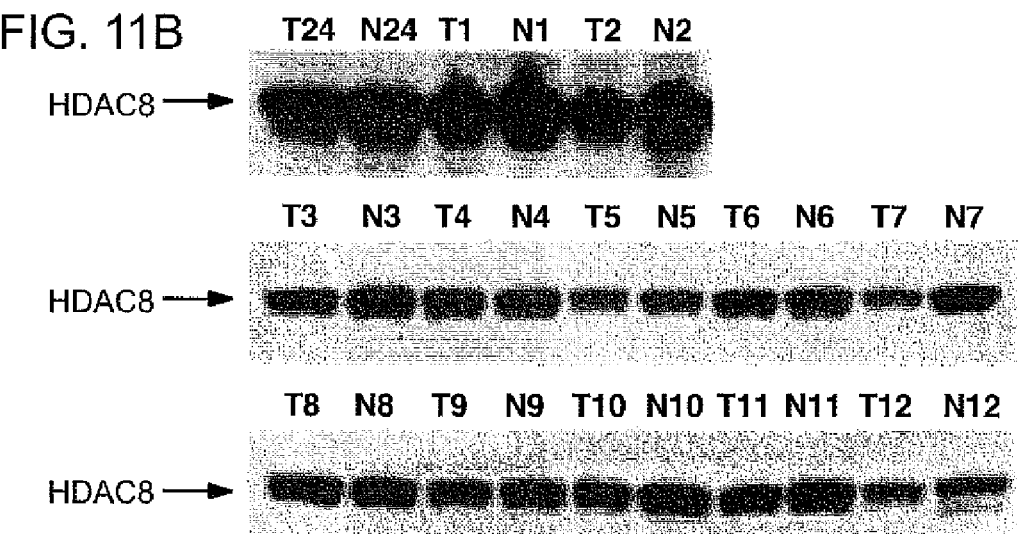

FIGS. 11A and 11B depict immunoblot analysis of HDAC8 expression in protein lysates from human DU-145, PC-3, and LNCaP prostate cancer cells (FIG. 11A); and analysis of HDAC8 in protein lysates from prostate cancer and normal prostate tissues (FIG. 11B).

DEFINITIONS

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, hut not limited to, murines, simians, humans, felines, canines, equines, bovines, mammalian farm animals, mammalian sport animals, and mammalian pets.

The terms "polynucleotide" and "nucleic acid" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

Hybridization reactions can be performed under conditions of different "stringency." Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 1×SSC (150 mM NaCl, 15 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. For example, high stringency conditions include aqueous hybridization (e.g., free of formamide) in 6×SSC (where 20×SSC contains 3.0 M NaCl and 0.3 M sodium citrate), 1% sodium dodecyl sulfate (SDS) at 65° C. for about 8 hours (or more), followed by one or more washes in 0.2×SSC, 0.1% SDS at 65° C. For example, moderate stringency conditions include aqueous hybridization (e.g., free of formamide) in 6×SSC, 1% SDS at 65° C. for about 8 hours (or more), followed by one or more washes in 2×SSC, 0.1% SDS at room temperature.

Stringent conditions for both DNA/DNA and DNA/RNA hybridization are as described by Sambrook et al. Molecular Cloning, A Laboratory Manual, 2nd Ed., Cold Spring Harbor Laboratory Press, Cold Spring Harbor, N.Y., 1989, herein incorporated by reference. For example, see page 7.52 of Sambrook et al.

As used herein, the term "isolated," in the context of a nucleic acid, is meant to describe a nucleic acid that is in an environment different from that in which the nucleic acid naturally occurs, or that is in an environment different from that which the nucleic acid was found. As used herein, an "isolated" nucleic acid is one that is substantially free of the nucleic acids or other macromolecules with which it is associated in nature. By substantially free is meant at least 50%, preferably at least 70%, more preferably at least 80%, and even more preferably at least 90% free of the materials with which it is associated in nature. As used herein, an "isolated" nucleic acid also refers to recombinant nucleic acids, which, by virtue of origin or manipulation: (1) are not associated with all or a portion of a nucleic acid with which it is associated in nature, (2) are linked to a nucleic acid other than that to which it is linked in nature, or (3) does not occur in nature.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a "recombinant host cell."

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein.

The term "binds specifically," in the context of antibody binding, refers to high avidity and/or high affinity binding of an antibody to a specific polypeptide i.e., epitope of an HDAC8 polypeptide. Antibody binding to an epitope on a specific HDAC8 polypeptide (also referred to herein as "an HDAC8 epitope") is preferably stronger than binding of the same antibody to any other epitope, particularly those which may be present in molecules in association with, or in the same sample, as the specific polypeptide of interest, e.g., binds more strongly to a specific HDAC8 epitope than to a different HDAC8 epitope so that by adjusting binding conditions the antibody binds almost exclusively to the specific HDAC8 epitope and not to any other HDAC8 epitope, and not to any other HDAC8 polypeptide which does not comprise the epitope.

Antibodies which bind specifically to an HDAC8 polypeptide or epitope may be capable of binding other polypeptides at a weak, yet detectable, level (e.g., 10% or less of the binding shown to the polypeptide of interest). Such weak binding, or background binding, is readily discernible from the specific antibody binding to an HDAC8 polypeptide or HDAC8 epitope e, e.g. by use of appropriate controls. In general, antibodies of the invention which bind to a specific HDAC8 polypeptide with a binding affinity of $10^{-7}$ M or more, e.g., $10^{-8}$ M, $10^{-9}$ M, or more are said to bind specifically to the specific HDAC8 polypeptide or HDAC8 epitope. In general, an antibody with a binding affinity of $10^{-6}$ M or less is not useful in that it will not bind an antigen at a detectable level using conventional methodology currently used.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

Detection methods of the invention may be qualitative or quantitative. Thus, as used herein, the terms "detection," "determination," and the like, refer to both qualitative and quantitative determinations, and include "measuring."

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an HDAC8 protein" includes a plurality of such proteins and reference to "the smooth muscle cell" includes reference to one or more smooth muscle cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of detecting smooth muscle cells, and cells undergoing differentiation to smooth muscle cells. The methods generally involve detecting HDAC8 mRNA and/or HDAC8 protein in a cell, e.g., a cell present in normal human tissue. The present invention is based in part on the observation that the expression of HDAC8 protein in normal human tissues is exclusively and specifically restricted to cells showing smooth muscle differentiation, including visceral and vascular smooth muscle cells, myofibroblasts, and myoepithelial cells. As such, detection of HDAC8 mRNA and/or HDAC8 protein is useful as a specific biomarker of smooth muscle cell differentiation.

The present invention further provides methods of identifying human tumors arising from smooth muscle cells. The methods generally involve detecting HDAC8 mRNA and/or HDAC8 protein in a cell. This aspect of the invention is based in part on the observation that detection of HDAC8 protein allows the pathological differential diagnosis between smooth muscle and non-smooth muscle tumors of the uterus and of the gastro-intestinal tract, or between tumors with smooth muscle differentiation and those without smooth muscle differentiation. An additional aspect of this invention pertains to the use of HDAC8 nucleic acid sequences and antibodies specific for the produced HDAC8 protein (or fragments thereof) for prognosis or susceptibility for certain disorders (e.g., uterus or intestinal tumors).

The present invention further provides methods for identifying agents that associate with HDAC8 protein in a cell. This aspect of the invention is based in part on the observation that HDAC8 protein is present mainly in the cytoplasm of cells showing smooth muscle differentiation. In addition, it was observed that HDAC8 protein physically interact with the smooth-muscle cytoskeleton protein smooth muscle α-actin. Accordingly, the present invention provides methods for identifying bioactive agents, such as proteins, that associate with HDAC8 protein.

The present invention farther provides methods and reagents for treating smooth muscle cell disorders. The methods generally involve administering to an individual in need thereof an agent that reduces the level of active HDAC8 protein in a smooth muscle cell. In some embodiments, the level of active HDAC8 is reduced by specifically inhibiting the production of HDAC8 protein, e.g., by inhibiting production of HDAC8 mRNA. This aspect of the invention is based in part on the observation that inhibition of HDAC8 protein dramatically reduces the contractile capacity of human vascular smooth muscle cells. A subject method provides for the specific inhibition of HDAC8 involved in smooth muscle contraction and thus provides a treatment for human smooth muscle cell disorders, including hypertension, asthma, atherosclerosis, myometrium and bladder hyperactivity, benign hyperplasia of the prostate, hypertrophic scars, and the like.

Methods of Detecting a Smooth Muscle Cell

The present invention provides methods of detecting smooth muscle cells, and cells undergoing differentiation to smooth muscle cells. The methods generally involve detecting HDAC8 mRNA and/or HDAC8 protein in a cell, e.g., a cell present in normal human tissue. The present invention is based in part on the observation that the expression of HDAC8 protein in normal human tissues is restricted to cells showing smooth muscle differentiation, including visceral and vascular smooth muscle cells, myofibroblasts, and myoepithelial cells. As such, detection of HDAC8 mRNA and/or HDAC8 protein is useful as a specific biomarker of smooth muscle cell differentiation.

The methods generally involve detecting HDAC8 mRNA and/or HDAC8 protein in a cell. Typically, the cell is in a biological sample that may include one or more smooth muscle cells. The biological sample is contacted with a detection agent that detects an HDAC8 mRNA or an HDAC8 polypeptide; and specific binding of the detection agent to a molecules) in the sample indicates the presence in the sample of a cell showing smooth muscle differentiation.

In many embodiments, HDAC8 mRNA is detected using a nucleic acid that hybridizes specifically to HDAC8 mRNA (or a nucleic acid complementary to HDAC8 mRNA, e.g., HDAC8 cDNA). The biological sample is contacted with a nucleic acid that hybridizes specifically to HDAC8 mRNA (or a nucleic acid complementary to HDAC8 mRNA); and specific binding of the HDAC8-specific nucleic acid to a molecule(s) (e.g., an HDAC8 mRNA or an HDAC8 cDNA) in the sample indicates the presence in the sample of a cell showing smooth muscle cell differentiation.

In many embodiments, HDAC8 polypeptides are detected using an immunological assay that employs an antibody specific for HDAC8 polypeptide. The biological sample is contacted with an antibody specific for an HDAC8 polypeptide; and specific binding of the anti-HDAC8 antibody to a molecule(s) (e.g., a protein) in the sample indicates the presence in the sample of a cell showing smooth muscle cell differentiation.

Smooth muscle cells that synthesize HDAC8 mRNA and/ or HDAC8 polypeptide, and that thus can be detected using a subject method include, but are not limited to, visceral smooth muscle cells; vascular smooth muscle cells, including large vessel (arteries and veins) smooth muscle cells, and microvessel (arterioles, venules, and capillaries) smooth muscle cells; myoepithelial cells; and myofibroblasts. Tissues and organs that contain HDAC8-producing smooth muscle cells include, but are not limited to, intestine, lung, fallopian tubes, and bladder. Glands that contain HDAC8-producing myoepithelial cells include, but are not limited to, mammary gland acini; mammary gland ducts; respiratory tract mucous glands; sweat glands; salivary glands; and skin eccrine glands. Tissues and organs that contain HDAC8-producing myofibroblasts include, but are not limited to, intestine (e.g., intestine subepithelial myofibroblasts); testis (e.g., testis peritubular myoid cells); lung (e.g., lung alveolar septae myofibroblasts); prostate (e.g., prostate stromal cells); spleen (e.g., reticular cells of the spleen); and ovary (e.g., external theca cells of the ovary).

HDAC8 mRNA and HDAC8 Polypeptides

As mentioned above, HDAC8 mRNA and/or HDAC8 polypeptides are detected in a biological sample; and the presence in the biological sample of HDAC8 mRNA or HDAC8 polypeptides indicates the presence of cells showing smooth muscle differentiation. The nucleotide sequences of HDAC8 mRNA of various species are known in the art and are publicly available. For example, nucleotide sequences of HDAC8 cDNA is available under GenBank Accession Nos. BC050433 (where the coding region is nucleotides 34-1167); NM_018486 (SEQ ID NO:1; where the coding region is nucleotides 43-1173); AJ277724 (where the coding region is nucleotides 43-1176); and AF245664 (where the coding region is nucleotides 10-1143).

Typically, nucleic acids are chosen such that other mRNA (or cDNA) other than HDAC8 mRNA (or cDNA) are not detected; for example, nucleic acids are chosen that do not substantially hybridize with HDAC mRNA (or cDNA) other than HDAC8. For example, after reverse transcribing HDAC8 m NA in a sample, HDAC8 cDNA is amplified using the following primers; 5'-CACCATGGAGGAGCCGGAG-GAA-3' (SEQ ID NO:2; GenBank NM_018486 bases 43-60) and 5'-GACCACATGCTTCAGATTCCCTT-3' (SEQ ID NO:3; complementary to bases 1173-1149 of the nucleotide sequence set forth in GenBank NM_018486), as described in Example 1.

The amino acid sequences of HDAC8 polypeptides of various species are known and are publicly available. For example, amino acid sequences of human HDAC8 are publicly available under GenBank Accession Nos. AAH50433, CAB90213, AAF73428, Q9BY41, and NP_060956. Antibodies that specifically bind HDAC8 polypeptides are readily generated. The entire HDAC8 polypeptide can be used as an immunogen to generate HDAC8-specific antibody. Alternatively, fragments of an HDAC8 polypeptide can be used to generate HDAC8-specific antibody.

Suitable HDAC8 fragments include fragments of from about 5 amino acids to about 150 amino acids in length, e.g., fragments of from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 75 amino acids, from about 75 amino acids to about 100 amino acids, from about 100 amino acids to about 125 amino acids, or from about 125 amino acids to about 150 amino acids in length, can be used to generate HDAC8-specific antibody. For example, a fragment of from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, or from about 40 amino acids to about 50 amino acids, of the N-terminal 50 amino acids of human HDAC8 polypeptide can be used to generate HDAC8-specific antibody. Alternatively, a fragment of from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, or from about 50 amino acids to about 70 amino acids in length, of the C-terminal 75 amino acids of HDAC8 can be used to generate HDAC8-specific antibody.

Anti-HDAC8 Antibody

Any known HDAC8-specific antibody can be used. In addition, anti-HDAC8 antibodies can be generated using all or a portion of an HDAC8 polypeptide. Methods of generating monoclonal and polyclonal antibodies are well known in the art. HDAC8-specific antibodies are commercially available. For example, suitable HDAC8-specific antibodies include: 1) mouse monoclonal HDAC8-specific antibody; product # H6412 (Sigma-Aldrich, St. Louis, Mo.); 2) rabbit polyclonal HDAC8-specific antibody, raised to a determinant within the amino-terminal 50 amino acids of HDAC8; product #AP1108a (Abgent, Inc., San Diego, Calif.); 3) rabbit polyclonal HDAC8-specific antibody, raised to a determinant within the carboxyl-terminal 50 amino acids of HDAC8; product #AP1108b (Abgent, Inc., San Diego, Calif.); 4) mouse monoclonal HDAC8-specific antibody, raised to full-length HDAC8; product # ab12176 (Abgent, Ltd., Cambridge, UK); 5) rabbit polyclonal HDAC8-specific antibody; product #3608-100 (BioVision, Mountain View, Calif.); 6) rabbit polyclonal HDAC8-specific antibody, raised to amino acids 305-377 of HDAC8; product #07-505 (Upstate, Lake Placid, N.Y.); and the like.

Detecting an HDAC8 Polypeptide in a Biological Sample

As mentioned above, in some embodiments, the presence in a biological sample of a cell showing smooth muscle differentiation is detected by detecting the presence of HDAC8 polypeptides in the biological sample. Thus, in some embodiments, the methods involve contacting a biological sample with a detection agent that specifically binds to an HDAC8 polypeptide; and detecting specific binding of the detection agent to a molecule(s) in the biological sample. Specific binding of the detection agent to an HDAC8 polypeptide in the biological sample indicates the presence in the sample of a cell showing smooth muscle differentiation.

The methods generally comprise:

a) contacting the sample with an antibody specific for an HDAC8 polypeptide; and b) detecting binding between the antibody and molecules of the sample.

Detection of specific binding of the HDAC8-specific antibody, when compared to a suitable control, is an indication that HDAC8 polypeptides, and thus cells showing smooth muscle differentiation, are present in the sample. Suitable controls include a sample known not to contain an HDAC8 polypeptide; and a sample contacted with an antibody not specific for HDAC8, e.g., an anti-idiotype antibody, an anti-actin antibody, and the like.

A variety of methods to detect specific antibody-antigen interactions are known in the art and can be used in the method, including, but not limited to, standard immunohistological methods, immunoprecipitation, an enzyme immunoassay, and a radioimmunoassay. In general, the HDAC8-specific antibody will be detectably labeled, either directly or indirectly. Direct labels include radioisotopes; enzymes whose products are detectable (e.g., luciferase, β-galactosidase, horse radish peroxidase, alkaline phosphatase, and the like); proteins that provide a detectable signal (e.g., a fluorescent protein, such as a green fluorescent protein (CFP) derived from *Aequoria victoria* or a derivative thereof; a GFP from another species such as *Renilla reniformis, Renilla mulleri*, or *Ptilosarcus guernyi*, as described in, e.g., WO 99/49019 and Peelle et al. (2001) J. Protein Chem. 20:507-519; any of a variety of fluorescent and colored proteins from Anthozoan species, as described in, e.g., Matz et al. (1999) Nature Biotechnol. 17:969-973; and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; and the like.

Where the antibody is detectably labeled, the antibody can be detected using an appropriate means, e.g., β-galactosidase can, depending on the substrate, yield colored product, which is detected spectrophotometrically, or a fluorescent product, which is detected with a fluorimeter; luciferase can yield a luminescent product detectable with a luminometer; etc.; radioactive labels are detected using x-ray film, scintillation counting, etc.; and the like.

The antibody may be attached (coupled) to an insoluble support, such as a polystyrene plate or a bead. Indirect labels include second antibodies specific for HDAC8-specific antibodies, wherein the second antibody is labeled as described above; members of specific binding pairs, e.g., biotin-avidin, and the like. The biological sample may be brought into contact with an antibody immobilized on a solid support or carrier, such as nitrocellulose, that is capable of immobilizing cells, cell particles, or soluble proteins. The support may then be washed with suitable buffers, followed by contacting with a detectably-labeled HDAC8-specific antibody. Detection methods are known in the art and will be chosen as appropriate to the signal emitted by the detectable label. Detection is generally accomplished in comparison to suitable controls, and to appropriate standards.

HDAC8 polypeptides can also be detected by staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

A variety of other reagents may be included in the detection assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

The detection methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times.

In many embodiments, a subject method comprises contacting a sample with an antibody specific for HDAC8. In some embodiments, the method includes an incubation step, in which antibody specific for HDAC8 is contacted with the biological sample for period of time (e.g., at ambient temperature, at 37° C., etc.), where the period of time is an incubation period of from about 1 minute to about 24 hours (e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 1 hours to about 4 hours, from about 4 hours to about 8 hours, from about 8 hours to about 16 hours, or from about 16 hours to about 24 hours). In some embodiments, following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound complexes (e.g., anti-HDAC8 antibody bound to HDAC8 protein) will then be detected.

Detecting an HDAC8 mRNA, or a Complement Thereof, in a Biological Sample

As mentioned above, in some embodiments, the presence in a biological sample of a cell showing smooth muscle differentiation is detected by detecting the presence of HDAC8 mRNA in the biological sample. Thus, in some embodiments, the methods involve contacting a biological sample with a detection agent that specifically binds to an HDAC8 mRNA (or a complement thereof e.g., an HDAC8 cDNA); and detecting specific binding of the detection agent to a molecule(s) in the biological sample. Specific binding of the detection agent to an HDAC8 mRNA in the biological sample indicates the presence in the sample of a cell showing smooth muscle differentiation. The detection agent is typically an HDAC8 polynucleotide that hybridizes to an HDAC8 mRNA or an HDAC8 cDNA.

Thus, in some embodiments, the methods generally comprise:

a) contacting the sample with an HDAC8 polynucleotide under conditions which allow hybridization; and b) detecting hybridization, if any.

Detection of hybridization, when compared to a suitable control, is an indication of the presence in the sample of an HDAC8 polynucleotide, and thus indicates the presence in the sample of a cell showing smooth muscle differentiation. Appropriate controls include, for example, a sample which is known not to contain HDAC8 mRNA, and use of a labeled polynucleotide of the same "sense" as an HDAC8 mRNA. Conditions which allow hybridization are known in the art, and have been described in more detail above. Detection can be accomplished by any known method, including, but not limited to, in situ hybridization, a polymerase chain reaction (PCR), reverse transcription-PCR(RT-PCR), and "Northern" or RNA blotting, or combinations of such techniques, using a suitably labeled HDAC8 polynucleotide. A variety of labels and labeling methods for polynucleotides are known in the art and can be used in the assay methods of the invention. Specific hybridization can be determined by comparison to appropriate controls.

In some embodiments, HDAC8 mRNA is detected by first making a cDNA copy of the HDAC8 mRNA, generating an HDAC8 cDNA; and amplifying the HDAC8 cDNA. Methods using PCR amplification can be performed on the DNA from a single cell, although it is convenient to use at least about $10^5$ cells. The use of the polymerase chain reaction is described in Saiki et al. (1985) Science 239:487, and a review of current techniques may be found in Sambrook, et al. Molecular Cloning: A Laboratory Manual, CSH Press 1989, pp. 14.2-14.33. A detectable label may be included in the amplification reaction. Suitable labels include fluorochromes, e.g. fluorescein isothiocyanate (FITC), rhodamine, Texas Red, phycoerythin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-PAM) or N,N,N',N'-tetramethyl-6-carboxyrhodamine (TORA), radioactive labels, e.g $^{32}P$, $^{35}S$, $^3H$, etc. The label may be a two-stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Methods of detecting HDAC8 mRNA will typically involve comparison of the nucleic acid abundance of a sample of interest with that of a control value to determine any relative differences, where the difference may be measured qualitatively and/or quantitatively, which differences are then related to the presence or absence of a cell showing smooth muscle differentiation. A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32; 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Isolated Primer Pairs

In some embodiments, the invention provides isolated nucleic acids that, under conditions that permit primer-initiated nucleic acid amplification, amplify an HDAC8 polynucleotide, e.g., a cDNA copy of an HDAC8 mRNA. The isolated nucleic acids that amplify an HDAC8 polynucleotide when used as primers in a polymerase chain reaction are from about 10 to about 20, from about 20 to about 30, from about 30 to about 40, from about 40 to about 50, from about 50 to about 100, or from about 100 to about 200 nucleotides in length. Generally, the nucleic acids are used in pairs in a polymerase chain reaction, where they are referred to as "forward" and "reverse" primers.

The first nucleic acid primer hybridizes under stringent hybridization conditions to a complementary nucleotide sequence in the target HDAC8 nucleic acid. The first nucleic acid primer comprises a nucleotide sequence that is at least about 75%, at least about 80%, at least about 85%, at least about 90%, at least about 95%, at least about 98%, at least about 99%, or 100% identical in nucleotide sequence to the complement of a nucleotide sequence of the same length in the target HDAC8 nucleic acid, where the target nucleic acid is an HDAC8 cDNA, e.g., comprising a nucleotide sequence as set forth in SEQ ID NO:1. The first nucleic acid primes synthesis of a first amplification product.

The second nucleic acid of the pair comprising a sequence of at least 10 contiguous nucleotides having from about 75% to about 100% sequence identity (e.g., least about 75%, at least about 80%, at least about 85%, at least about 90%, at least about 95%, at least about 98%, or at least about 99% nucleotide sequence identity, or 100% nucleotide sequence identity) to the reverse complement of the nucleic acid sequence set forth in SEQ ID NO:1; and primes the synthesis of a second amplification product having a nucleotide sequence that is complementary to the first amplification product.

Thus, in some embodiments, the invention provides a pair of isolated nucleic acids, each from about 10 to 200 nucleotides in length, the first nucleic acid of the pair comprising a sequence of at least 10 contiguous nucleotides having from about 75% to about 100% sequence identity to the nucleic acid sequence set forth in SEQ ID NO:1 (GenBank NM_018486) and the second nucleic acid of the pair comprising a sequence of at least 10 contiguous nucleotides having from about 75% to about 100% sequence identity to the reverse complement of the nucleic acid sequence set forth in SEQ ID NO:1, wherein the sequence of the second nucleic acid is located 3, of the nucleic acid sequence of the first nucleic acid in SEQ ID NO:1, and where the nucleic acid pair primes the synthesis of an amplification product that is from about 20 nucleotides to about 1130 nucleotides in length. The primer nucleic acids are prepared using any known method, e.g., automated synthesis, and the like.

In some embodiments, the first and/or the second nucleic acid comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^3H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In general, the first and second nucleic acids are chosen such that the amplified product has a length of from about 20 nucleotides to about 1130 nucleotides in length, e.g., from about 20 nucleotides to about 50, from about 50 nucleotides to about 75 nucleotides, from about 75 nucleotides to about 100 nucleotides, from about 100 nucleotides to about 125 nucleotides, from about 125 nucleotides to about 150 nucleotides, from about 150 nucleotides to about 175 nucleotides, from about 175 nucleotides to about 200 nucleotides, from about 200 nucleotides to about 250 nucleotides, from about 250 nucleotides to about 300 nucleotides, from about 300 nucleotides to about 350 nucleotides, from about 350 nucleotides to about 500 nucleotides, from about 500 nucleotides to about 750 nucleotides, from about 750 nucleotides to about 1000 nucleotides, or from about 1000 nucleotides to about 1130 nucleotides in length.

The following are non-limiting examples of suitable primer pairs: 1) 5'-CACCATGGAGGAGCCGGAGGAA-3' (SEQ ID NO:2; including bases 43-60 of SEQ ID NO:1) and 5'-GACCACATGCTTCAGATTCCCTT-3' (SEQ ID NO:3; complementary to bases 1173-1149 of the nucleotide sequence set forth in SEQ ID NO:1); 2) 5'-ATGGAGGAGC-CGGAGGAACCGG-3'(SEQ ID NO:4) and 5'-ACATGCT-TCAGATTCCCTTTGAT-3'(SEQ ID NO:5); 3) 5'-GAG-GAGCCGGAGGAACCGGCGG-3'(SEQ ID NO:6) and 5'-GCTTCAGATTCCCTTTGATGTAG-3' (SEQ ID NO:7).

Conditions that permit primer-initiated nucleic acid amplification are well known to those skilled in the art, and include the presence of a DNA polymerase; deoxynucleotide triphosphates; and magnesium ions. Suitable reaction conditions are well known to those skilled in the art of nucleic acid amplification. Exemplary, non-limiting reaction conditions are described in the Examples. The DNA polymerase is generally one that has high affinity for binding at the 3'-end of an oligonucleotide hybridized to a nucleic acid strand. The DNA polymerase is generally one that has little or no 5'→3' exonuclease activity so as to minimize degradation of primer, termination or primer extension polynucleotides. The DNA polymerase is generally one that has little to no proofreading activity. In many embodiments, the DNA polymerase is thermostable, e.g., is catalytically active at temperatures in excess of about 75° C. DNA polymerases that are suitable for use in a subject method include, but are not limited to, DNA polymerases discussed in U.S. Pat. Nos. 5,648,211 and 5,744,312, which include exo$^-$ Vent (New England Biolabs), exo$^-$ Deep Vent (New England Biolabs), Bst (BioRad), exo$^-$ Pfu (Stratagene), Bea (Panvera), sequencing grade Taq (Promega); thermostable DNA polymerases from *Thermoanaerobacter thermohydrosusfuricus*; and the like. In some embodiments, the reaction mixture includes an RNAse H.

Magnesium ions are typically present in the reaction mix in a concentration of from about 1 mM to about 100 mM, e.g., from about 1 mM to about 3 mM, from about 3 mM to about 5 mM, from about 5 mM to about 10 mM, from about 10 mM to about 25 mM, from about 25 mM to about 50 mM, from about 50 mM to about 75 mM, or from about 75 mM to about 100 mM.

Usually the reaction mixture will comprise four different types of dNTPs corresponding to the four naturally occurring bases are present, i.e. dATP, dTTP, dCTP and dGTP. In the subject methods, each dNTP will typically be present at a final concentration in the reaction, ranging from about 10 µM to 5000 µM, e.g., from about 10 µM to about 50 µM, from about 50 µM to about 100 µM, from about 100 µM to about 200 µM, from about 200 µM to about 500 µM, from about 500 µM to about 1000 µM, from about 1000 µM to about 2000 µM, from about 2000 µM to about 3000 µM, from about 3000 µM to about 4000 µM, or from about 4000 µM to about 5000 µM. In many embodiments, each dNTP will be present at a final concentration in the reaction of from about 20 µM to 1000 µM, from about 100 µM to about 200 µM, or from about 50 µM to about 200 µM.

The reaction mixture may further include an aqueous buffer medium that includes a source of monovalent ions, a source of divalent cations and a buffering agent. Any convenient source of monovalent ions, such as KCl, K-acetate, Nit-acetate, K-glutamate, NH$_4$Cl, ammonium sulfate, and the like may be employed. The divalent cation may be magnesium, manganese, zinc and the like, where the cation will typically be magnesium. Any convenient source of magnesium cation may be employed, including MgCl$_2$, Mg-acetate, and the like. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, e.g., pH 7.3 at 72° C. Other agents which may be present in the buffer medium include chelating agents, such as EDTA, EGTA and the like.

Each primer nucleic acid is present in the reaction mixture at a concentration of from about 50 nM to about 900 nM, e.g., the 37 primer and the 5' primer nucleic acid are each independently present at a concentration of from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 400 nM, from about 400 nM to about 500 nM, from about 500 nM to about 600 nM, from about 600 nM to about 700 nM, from about 700 nM to about 800 nM, or from about 800 nM to about 900 nM.

Kits

The detection methods can be provided as part of a kit. Thus, the invention further provides kits for detecting the presence and/or a level of an HDAC8 polypeptide or an HDAC8 polynucleotide in a biological sample. Procedures using these kits can be performed by clinical laboratories, experimental laboratories, medical practitioners, or private individuals. The kits of the invention for detecting an HDAC8 polypeptide comprise a moiety that specifically binds an HDAC8 polypeptide, including, but not limited to, an HDAC8-specific antibody. The kits of the invention for detecting an HDAC polynucleotide comprise a moiety that specifically hybridizes to an HDAC8 polynucleotide. The kit may optionally provide additional components that are useful in the procedure, including, but not limited to, buffers, developing reagents, labels, reacting surfaces, means for detections, control samples, standards, instructions, and interpretive information.

The invention further provides a kit comprising a pair of nucleic acids as described above. The nucleic acids are present in a suitable storage medium, e.g., buffered solution, typically in a suitable container. The components of the instant kit can be in solution or lyophilized as appropriate. The kit includes the pair of nucleic acids, and may further include a buffer; reagents for polymerase chain reaction (e.g., deoxynucleotide triphosphates (dATP, dTTP, dCTP, and dGTP), a thermostable DNA polymerase, a buffer suitable for polymerase chain reaction, a solution containing Mg$^{2+}$ ions (e.g., MgCl$_2$), and other components well known to those skilled in the art for carrying out a polymerase chain reaction). The kit may further include instructions for use of the kit, which instructions may be provided in a variety of forms, e.g., as printed information, on a compact disc, and the like. The kit may further include reagents necessary for extraction of mRNA from a biological sample (e.g., biopsy sample, blood, and the like) from an individual. In some embodiments, the kit will include components necessary for reverse transcription of mRNA. The kits are useful in diagnostic applications, as described herein.

Detecting Cancerous Cells

The present invention provides methods of detecting cancerous cells in a biological sample, where the cancerous cell is one that produces a lower than normal level, or a higher than normal level, of HDAC8 mRNA and/or protein, compared to a normal (non-cancerous) cell of the same cell type.

The methods generally involve detecting an HDAC8 mRNA (or cDNA) and/or an HDAC8 polypeptide in a biological sample, as described above. Where the HDAC8 mRNA or HDAC8 polypeptide level is lower or higher than the HDAC8 mRNA or HDAC8 polypeptide level in a normal cell of the same cell type, the sample may contain a cancerous cell. In some embodiments, where the level of HDAC8 mRNA and/or HDAC8 polypeptide in a test cell is from about 5% to about 50% or more, lower than the level of HDAC8 mRNA and/or HDAC8 polypeptide in a normal cell of the same cell type, the test cell may be cancerous. In other embodiments, where the level of HDAC8 mRNA and/or HDAC8 polypeptide in a test cell is from about 25% to about 50%, from about 50% to about 100%, from about 2-fold to about 10-fold, or from about 10-fold to about 100-fold, or more, higher than the level of HDAC8 mRNA and/or HDAC8 polypeptide in a normal cell of the same cell type, the test cell may be cancerous.

The methods allow discrimination between a cancerous cell and normal cell of the same cell type. The methods also allow staging of a cancer. The methods also allow a determination of whether a given cancer treatment is efficacious in treating the cancer.

Cancerous cells that can be detected using a subject method are cancerous cells arising from smooth muscle cells. Cancerous cells that can be detected using a subject method include, but are not limited to, benign or malignant tumors originating either from smooth muscle cells or like cells from any organ or tissue, such as uterine tumors of stromal cell origin (e.g., uterine leiomyosarcoma); intestinal tumors of stromal cell origin (including gastrointestinal stromal tumor cells); vascular wall tumors (including leiomyomas and leiomyosarcomas); and tumors from any cell type with smooth muscle differentiation (e.g., uterine endometrial stroma sarcoma with smooth muscle differentiation); and the like.

The present invention provides methods of determining whether a given cancer treatment is effective to reduce tumor growth and/or reduce tumor load of a tumor of smooth muscle cell origin. The methods generally involve contacting a cancerous cell of smooth muscle cell origin with an anti-cancer agent; and detecting the level of HDAC8 mRNA and/or protein in the cancerous cell. If the level of HDAC8 mRNA and/or HDAC8 protein increases or decreases in the cell following contact with the anti-cancer agent, such that the level of HDAC8 mRNA and/or HDAC8 protein approaches the level found in a corresponding normal cell, the anti-cancer agent is considered effective in treating the cancer.

Treatment Methods

The present invention provides methods of treating smooth muscle cell disorders. The methods generally involve administering to an individual in need thereof an effective amount of an agent that reduces a level of active HDAC8 in a smooth muscle cell in the individual.

An effective amount of an agent that reduces a level of active HDAC8 in a smooth muscle cell is an amount that reduces a level of active HDAC8 in a smooth muscle cell by at least about 5%, at least about 10%, at least about 15%, at least about 20%, at least about 25%, at least about 30%, at least about 40%, at least about 50%, at least about 60%, at least about 70%, at least about 80%, or more, compared with the level of active HDAC8 in the cell in the absence of the agent. The term "reducing a level of active HDAC8" includes reducing a level of HDAC8 mRNA, reducing a level of HDAC8 polypeptide, and reducing a level of HDAC8 enzymatic activity.

Smooth muscle disorders that are amenable to treatment with a subject method include GI tract motility disorders, such as Hirschprung's disease, duodenal atresia, chronic intestinal pseudo-obstruction; hypertension; asthma; atherosclerosis; benign hyperplasia of the prostate; irritable bowel syndrome; erectile dysfunction; urinary urgency; myometrium hyperactivity; bladder overactivity; acute kidney dilation dut to obstruction by urolithiasis; tendon fibrosis (e.g., Dupuytren's disease, Ledderhose disease, etc.); penile induration (La Peyronie disease); fibrosis in various tissues; and hypertrophic scars.

Active Agents

The present invention provides active agents that reduce a level of active HDAC8, e.g., agents that reduce a level of HDAC8 mRNA, agents that reduce a level of HDAC8 polypeptide, and agents that reduce a level of HDAC8 enzymatic activity, in a smooth muscle cell. Such agents are useful to treat smooth muscle cell disorders.

Small Molecule Agents

In many embodiments, the agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

Nucleic Acid Agents

In some embodiments, an active agent is a nucleic acid. Suitable nucleic acids that reduce a level of active HDAC8 in a smooth muscle cell include non-translated RNAs, such as an antisense RNA, a ribozyme, an RNAi and an siRNA. Interfering RNA (RNAi) fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORE, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

In some embodiments, an siRNA comprises the sequences 5'-UGAGCCCCACCGAAUCCAATT-3' (SEQ ID NO:8) and 5'-UUGGAUUCGGUGGGCCUCATT-3' (SEQ ID NO:9). In some embodiments, an siRNA comprises the sequences 5'-ACGGGCCAGUAUGGUGCAUTT-3' (SEQ ID NO:10) and 5'-AUGCACCAUACUGGCCCGUTT-3' (SEQ ID NO:11).

The present invention provides nucleic acids that comprise a nucleotide sequence that encodes an siRNA as described above, which nucleotide sequence is operably linked to a promoter that is functional in a eukaryotic cell, e.g., a cell that exhibits smooth muscle differentiation; e.g., a smooth muscle cell. The present invention further provides vectors, including expression vectors, which include a subject siRNA-encoding nucleic acid; and host cells that harbor a subject nucleic acid or a subject expression vector.

A subject siRNA-encoding nucleic acid comprises, in order from 5' to 3' and in operable linkage, a promoter functional in a smooth muscle cell, and a nucleotide sequence that encodes an siRNA that, when produced in the smooth muscle cell, reduces the level of HDAC8 mRNA and/or HDAC8 protein in the cell.

In some embodiments, the promoter is an inducible promoter, e.g., the target cell-specific promoter includes one or more regulatory elements that confer inducible transcriptional control on an operably linked coding region. Inducible promoters and control elements are known in the art and include, but are not limited to, an androgen-inducible promoter; a hormone-inducible promoter; a heavy metal inducible promoter; and the like.

A subject nucleic acid comprises an siRNA coding sequence operably linked to a promoter. A subject nucleic acid comprises a nucleic acid that encodes an siRNA (also referred to herein as "an siRNA agent"). Suitable siRNA agents include siRNA agents that modulate expression of a target HDAC8 gene by an RNA interference mechanism. A "small interfering" or "short interfering RNA" or siRNA is a RNA duplex of nucleotides that is targeted to a gene interest (a "target gene" or a "target coding sequence"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted HDAC8 gene. In some embodiments, the length of the duplex of siRNAs is less than 30 nucleotides. In some embodiments, the duplex can be 29 nucleotides (nt), 28 nt, 27 nt, 26 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5 nt, 6 nt, 7 nt, 8 nt, 9 nt, 10 nt, 11 nt, 12 nt, or 13 nucleotides in length. The hairpin structure can also contain 3' or 5' overhang portions. In some embodiments, the overhang is a 3' or a 5' overhang 0 nt, 1 nt, 2 nt, 3 nt, 4 nt, or 5 nucleotides in length.

In some embodiments, a subject nucleic acid agent comprises a nucleotide sequence encoding an siRNA that, when produced in a eukaryotic cell, reduces the level of HDAC8 mRNA and/or protein in the cell. In some embodiments, a subject siRNA-encoding nucleic acid comprises the nucleotide sequence 5'-TGAGCCCCACCGAATCCAA(X)$_n$TTG-GATTCGGTGGGGCTCA-3' (SEQ ID NO:12; where X is any nucleotide and n is an integer from 1 to 10). In some embodiments, a subject siRNA-encoding nucleic acid comprises the nucleotide sequence 5'-TGAGCCCCAC-CGAATCCAATTTTTGCTTGGATTCG-GTGGGGCTCATT-3' (SEQ ID NO:13). In some embodiments, a subject siRNA-encoding nucleic acid comprises the nucleotide sequence 5'-ACGGGCCAGTATGGT-GCAT(X)$_n$ATGCACCATACTGGCCCGT-3' (SEQ ID NO:14; where X is any nucleotide and n is an integer from 1 to 10). In some embodiments, a subject siRNA-encoding nucleic acid comprises the nucleotide sequence 5'-ACGGGCCAGTATGGTGCATTTTGCATG-CACCATACTGGCCCGT-3' (SEQ ID NO:15).

Preparing a Subject Nucleic Acid

Preparation of a subject nucleic acid accomplished utilizing any of the methods known to one skilled in the art. Changes in nucleotide sequence of any given nucleic acid is accomplished by any of various standard methods, including site-specific mutagenesis, polymerase chain reaction (PCR) amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Berger and Kimmel, Guide to Molecular Cloning Techniques, Methods in Enzymology, Volume 152 Academic Press, Inc., San Diego, Calif. merger); Sambrook et al., Molecular Cloning—A Laboratory Manual (2nd ed.) Vol. 1-3, Cold Spring Harbor Laboratory, Cold Spring Harbor Press, N.Y., (Sambrook) (1989); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel); Pirrung et al., U.S. Pat. No. 5,143,854; and Fodor et al., Science, 251:767-77 (1991). Using these techniques, it is possible to insert or delete, at will, a polynucleotide of any length into a subject nucleic acid.

A subject nucleic acid, or a fragment of a subject nucleic acid, will in some embodiments be prepared using chemical synthesis of linear oligonucleotides which may be carried out utilizing techniques well known in the art. The synthesis method selected will depend on various factors including the length of the desired nucleic acid and such choice is within the skill of the ordinary artisan. Oligonucleotides are typically synthesized chemically according to the solid phase phosphoramidite triester method described by Beaucage and Caruthers, Tetrahedron Letts., 22(20):1859-1862 (1981), e.g., using an automated synthesizer, as described in Needham-VanDevanter et al., Nucleic Acids Res., 12:6159-6168 (1984). Oligonucleotides can also be custom made and ordered from a variety of commercial sources known to persons of skill in the art.

Synthetic linear oligonucleotides maybe purified by polyacrylamide gel electrophoresis, or by any of a number of chromatographic methods, including gel chromatography and high pressure liquid chromatography. The sequence of the synthetic oligonucleotides can be verified using the chemical degradation method of Maxam and Gilbert in Grossman and Moldave (eds.) Academic Press, New York, Methods in Enzymology, 65:499-560 (1980). If modified bases are incorporated into the oligonucleotide, and particularly if modified phosphodiester linkages are used, then the synthetic procedures are altered as needed according to known procedures. In this regard, Uhlmann, et al., Chemical Reviews, 90:543-584 (1990) provide references and outline procedures for making oligonucleotides with modified bases and modified phosphodiester linkages. Sequences of short oligonucleotides can also be analyzed by laser desorption mass spectroscopy or by fast atom bombardment (McNeal, et al., J. Am. Chem. Soc., 104; 976 (1982); Viari, et al., Biomed. Enciron. Mass Spectrom., 14:83 (1987); Grotjahn et al., Nuc. Acid Res., 10:4671 (1982)).

Linear oligonucleotides may also be prepared by polymerase chain reaction (PCR) techniques as described, for example, by Saiki et al., Science, 239:487 (1988). In vitro amplification techniques suitable for amplifying nucleotide sequences are also well known in the art. Examples of such techniques including the polymerase chain reaction (PCR), the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; PCR Protocols A Guide to Methods and Applications (Inis et al., eds) Academic Press Inc., San Diego, Calif. (1990) (Innis); Arnheim & Levinson (Oct. 1, 1990) C&EN 36-47; The Journal Of NIH Research, 3:81-94 (1991); (Kwoh et al., (1989) Proc. Natl. Acad. Sci. USA, 86:1173; Guatelli et al., Proc. Natl. Acad. Sci. USA, 87:1874 (1990); Lomell et al., J. Clin. Chem., 35:1826 (1989); Landegren et al., Science, 241:1077-1080 (1988); Van Brunt, Biotechnology, 8:291-294 (1990); Wu and Wallace, Gene, 4:560 (1989); Barringer et al., Gene, 89:117 (1990), and Sooknanan and Malek, Biotechnology, 13:563-564 (1995). Improved methods of cloning in vitro amplified nucleic acids are described in Wallace et al., U.S. Pat. No. 5,426,039.

Recombinant Vectors

The above nucleic acid constructs comprising an siRNA coding domain operably linked to a promoter are, in many embodiments, present in a vector. A vector that comprises a subject nucleic acid is referred to herein as a "recombinant vector." The constructs may be present on any convenient type of vector, where representative vectors of interest include, but are not limited to: plasmid vectors, viral vectors, and the like.

Certain types of vectors allow the expression cassettes of the present invention to be amplified. Other types of vectors are necessary for efficient introduction of subject nucleic acid to cells and their stable expression once introduced. Any vector capable of accepting a subject nucleic acid is contemplated as a suitable recombinant vector for the purposes of the invention. The vector may be any circular or linear length of DNA that either integrates into the host genome or is maintained in episomal form. Vectors may require additional manipulation or particular conditions to be efficiently incorporated into a host cell (e.g., many expression plasmids), or can be part of a self-integrating, cell specific system (e.g., a recombinant virus). The vector is in some embodiments functional in a prokaryotic cell, where such vectors function to propagate the recombinant vector. The vector is in some embodiments functional in a eukaryotic cell, where the vector will in many embodiments be an expression vector.

Representative eukaryotic plasmid vectors of interest include, for example; pCMVneo, pShuttle, pDNR and Ad-X (Clontech Laboratories, Inc.); as well as BPV, EBV, vaccinia, SV40, 2-micron circle, pcDNA3.1, pcDNA3.1/GS pYES2/GS, pMT, p IND, pIND(Spl), pVgRXR, and the like, or their derivatives. Such plasmids are well known in the art (Botstein et al., Miami Wntr. SyTnp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et at., J. Clin. Hematol. Oncol. 10:39-48, 1980; Maniatis, In: Cell Biology; A Comprehensive Treatise, Vol. 3, Gene Sequence Expression, Academic Press, NY, pp. 563-608, 1980.

Certain vectors, "expression vectors," are capable of directing the expression of genes. Any expression vector comprising an expression cassette of the present invention qualifies as an expression cassette of the present invention. In general, expression vectors of utility in recombinant DNA techniques often are in the form of plasmids. In some embodiments, a subject vector is a viral vector, e.g., replication defective retroviruses, lentiviruses, adenoviruses; adeno-associated viruses (e.g., AAV-1, AAV-2, etc.; baculovirus, CAMV, herpesviruses; vaccinia virus; and the like.

Examples of suitable prokaryotic expression vectors that can be engineered to accept a subject nucleic acid include pTrc (Amann et al., Gene, 69:301-315 (1988)) and pBluescript (Stratagene, San Diego, Calif.). Examples of vectors for expression in yeast *S. cerevisiae* include pYepSec1 (Baldari et al., EMBO J., 6:229-234 (1987)), pMFa (Kurjan and Herskowitz, Cell, 30:933-943 (1982)), pJRY88 (Schultz et al., Gene, 54:113-123 (1987)), pYES2 (Invitrogen, Carlsbad, Calif.), and pPicZ (Invitrogen, Carlsbad, Calif.). Baculovirus vectors are often used for expression of dsRNAs in cultured insect cells (e.g., Sf9 cells see, U.S. Pat. No. 4,745,051) and include the pAc series (Smith et al., Mol. Cell. Biol., 3:2156-2165 (1983)), the pVL series (Lucklow and Summers, Virology, 170:31-39 (1989)) and pBlueBac (available from Invitrogen, San Diego).

Infection of cells with a viral vector will in some embodiments be used for introducing expression cassettes of the present invention into cells. The viral vector approach has the advantage that a large proportion of cells receive the expression cassette, which can obviate the need for selection of cells that have been successfully transfected. Exemplary mammalian viral vector systems include retroviral vectors, lentiviral vectors, adenoviral vectors, adeno-associated type 1 ("AAV-1") or adeno-associated type 2 ("AAV-2") vectors, hepatitis delta vectors, live, attenuated delta viruses, and herpes viral vectors.

In some embodiments, a subject recombinant vector is a retroviral vector. Retroviruses are RNA viruses that are useful for stably incorporating genetic information into the host cell genome. When a retrovirus infects cells, their RNA genomes are converted to a dsDNA form (by the viral enzyme reverse transcriptase). The viral DNA is efficiently integrated into the host genome, where it permanently resides, replicating along with host DNA at each cell division. The integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely. Retroviruses are therefore attractive vectors because they can permanently express a foreign gene in cells. Most or possibly all regions of the host genome are accessible to retroviral integration (Withers-Ward et al., Genes Dev., 8:1473-1487 (1994)). Moreover, they can infect virtually every type of mammalian cell, making them exceptionally versatile.

Retroviral vector particles are prepared by recombinantly inserting a subject nucleic acid into a retroviral vector and packaging the vector with retroviral proteins by use of a packaging cell line or by co-transfecting non-packaging cell lines with the retroviral vector and additional vectors that express retroviral proteins. The resultant retroviral vector particle is generally incapable of replication in the host cell and is capable of integrating into the host cell genome as a proviral sequence containing the expression cassette containing a nucleic acid encoding an siRNA. As a result, the host cell produces the siRNA encoded by the subject recombinant expression vector.

Packaging cell lines are generally used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by introducing into a cell line one or more expression plasmids encoding the appropriate core and envelope proteins. In these cells, the gag, pol, and env genes can be derived from the same or different retroviruses.

A number of packaging cell lines suitable for the present invention are available in the art. Examples of these cell lines include Crip, GPE86, PA317 and PG13. See, e.g., Miller et al., J. Virol., 65:2220-2224 (1991). Examples of other packaging cell lines are described in Cone and Mulligan, Proceedings of the National Academy of Sciences, U.S.A., 81:6349-6353 (1984) and in Danos and Mulligan, Proceedings of the National Academy of Sciences, U.S.A., 85:6460-6464 (1988); Eglitis et al., Biotechniques, 6:608-614 (1988); Miller et al., Biotechniques, 7:981-990 (1989). Amphotropic or xenotropic envelope proteins, such as those produced by PA317 and GPX packaging cell lines may also be used to package the retroviral vectors.

Defective retroviruses are well characterized for use in gene transfer to mammalian cells (for a review see Miller, A. D., Blood, 76:271 (1990)). A recombinant retrovirus can be constructed having a subject nucleic acid inserted into the retroviral genome. Additionally, portions of the retroviral genome can be removed to render the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals.

Examples of suitable retroviruses include pLJ, pZIP, pWE and pEM which are well known to those skilled in the art. Examples of suitable packaging virus lines include ψCrip, ψCre, ψ2, and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al., Science, 230:1395-1398 (1985); Danos and Mulligan, Proc. Natl. Acad. Sci. USA, 85:6460-6464 (1988); Wilson et al., Proc. Natl. Acad. Sci. USA, 85:3014-3018 (1988); Armentano et al., Proc. Natl. Acad. Sci. USA, 87:6141-6145 (1990); Huber et al., Proc. Natl. Acad. Sci. USA, 88:8039-8043 (1991); Ferry et al., Proc. Natl. Acad. Sci. USA, 88:8377-8381 (1991); Chowdhury et al., Science, 254:1802-1805 (1991); van Beusechem et al., Proc. Natl. Acad. Sci. USA, 89:7640-7644 (1992); Kay et al., Human Gene Therapy, 3:641-647 (1992); Dai et al., Proc. Natl. Acad. Sci. USA, 89:10892-10895 (1992); Hwu et al., J. Immunol., 150:4:104-115 (1993); U.S. Pat. No. 4,868,116; U.S. Pat. No. 4,980,286; PCT Application WO 89/07136; PCT Application WO 89/02468; PCT Application WO 89/05345; and PCT Application WO 92/07573; EPA 0 178 220; U.S. Pat. No. 4,405,712; Gilboa, Biotechniques, 4:504-512 (1986); Mann et al., Cell, 33:153-159 (1983); Cone and Mulligan, Proc. Natl. Acad. Sci. USA, 81:6349-6353 (1984); Eglitis et al., Biotechniques 6:608-614 (1988); Miller et al., Biotechniques, 7:981-990 (1989); Miller, Nature (1992), supra; Mulligan, Science, 260:926-932 (1993); and Gould et al., and International Patent Application No. WO 92/07943 entitled "Retroviral Vectors Useful in Gene Therapy.").

The genome of an adenovirus can be manipulated such that it includes a subject nucleic acid, but is inactivated in terms of its ability to replicate in a normal lytic viral life cycle. See for example Berkner et al., BioTechniques, 6:616 (1988); Rosenfeld et al., Science, 252:431-434 (1991); and Rosenfeld et al., Cell, 68:143-155 (1992). Suitable adenoviral vectors derived from the adenovirus strain Ad type 5 d1324 or other strains of adenovirus (e.g., Adz, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al., Proc. Natl. Acad. Sci. USA, 89):6482-6486 (1992)), hepatocytes (Herz and Gerard, Proc. Natl. Acad. Sci. USA, 90:2812-2816 (1993)) and muscle cells (Quantin et al., Proc. Natl. Acad. Sci. USA, 89:2581-2584 (1992)).

Adeno-associated virus (AAV) is a naturally occurring defective virus that requires another virus, such as an adenovirus or a herpes virus, as a helper virus for efficient replication and a productive life cycle. (For a review see Muzyczka et al., Curr. Topics in Micro. and Immunol., 158:97-129 (1992)). It exhibits a high frequency of stable integration (see for example Flotte et al., Am. J. Respir. Cell. Mol. Biol., 7:349-356 (1992); Samulski et al., J. Virol., 63:3822-3828 (1989); and McLaughlin et al., J. Virol, 62:1963-1973 (1989); Flotte, et al., Gene Ther., 2:29-37 (1995); Zeitlin, et al., Gene Ther, 2:623-31 (1995); Baudard, et al., Hum. Gene Ther., 7:1309-22 (1996)). Vectors containing as little as 300 base pairs of AAV can be packaged and can integrate. Space for exogenous nucleic acid is limited to about 4.5 kb, well in excess of the overall size of the expression vectors of the invention. An AAV vector, such as that described in Tratschin et al., Mol. Cell. Biol., 5:3251-3260 (1985) can be used to introduce the expression vector into cells. A variety of nucleic acids have been introduced into different cell types using AAV vectors (see for example Hermonat et al., Proc. Natl. Acad. Sci. USA, 81:6466-6470 (1984); Tratschin et al., Mol. Cell. Biol., 4:2072-2081 (1985); Wondisford et al., Mol. Endocrinol., 2:32-39 (1988); Tratschin et al., J. Virol., 51:611-619 (1984); and Flotte et al., J. Biol. Chem., 268: 3781-3790 (1993)).

A subject nucleic acid will in some embodiments be incorporated into lentiviral vectors. In this regard, see: Qin et al. (2003) Proc. Natl. Acad. Sci. USA 100: 183-188; Miyoshi et al. (1998) J. Virol. 72: 8150-8157; Tisconia et al. (2003) Proc. Natl. Acad. Sci. USA 100: 1844-1848; and Pfeifer et al. (2002) Proc. Natl. Acad. Sci. USA 99: 2140-2145. Lentiviral vector kits are available from Invitrogen (Carlsbad, Calif.).

A subject recombinant vector will in some embodiments include one or more selectable markers. A number of selection systems may be used, including but not limited to the herpes simplex virus thymidine kinase (Wigler, et al., Cell, 11:223 (1977)), hypoxanthine-guanine phosphoribosyltransferase (Szybalska & Szybalski, Proc. Natl. Acad. Sci. USA, 48:2026 (1962)), and adenine phosphoribosyltransferase (Lowy et al., Cell, 22:817 (1980)) genes can be employed in tk⁻, hgprt⁻ or aprt⁻ cells, respectively. Also, antimetabolite resistance can be used as the basis of selection for dhfr, which confers resistance to methotrexate (Wigler et al., Natl. Acad. Sci. USA, 77:3567 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418 (Colberre-Garapin et al., J. Mol. Biol., 150:1 (1981)); and hygro, which confers resistance to hygromycin (Santerre, et al., Gene, 30:147 (1984)). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047 (1988)); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Introducing a Recombinant Vector into a Host Cell

A subject recombinant vector may be introduced into a host cell utilizing a vehicle, or by various physical methods. Representative examples of such methods include transformation using calcium phosphate precipitation (Dubensky et al., PNAS, 81:7529-7533 (1984)), direct microinjection of such nucleic acid molecules into intact target cells (Acsadi et al., Nature, 352:815-818 (1991)), and electroporation whereby cells suspended in a conducting solution are subjected to an intense electric field in order to transiently polarize the membrane, allowing entry of the nucleic acids. Other procedures include the use of nucleic acid molecules linked to an inactive adenovirus (Cotton et al., PNAS, 89; 6094 (1990)), lipofection (Felgner et al., Proc. Natl. Acad. Sci. USA, 84:7413-7417 (1989)), microprojectile bombardment (Williams et al., PNAS, 88:2726-2730 (1991)), polycation compounds such as polylysine, receptor specific ligands, liposomes entrapping the nucleic acid molecules, and spheroplast fusion whereby E. coli containing the nucleic acid molecules are stripped of their outer cell walls and fused to animal cells using polyethylene glycol.

Peptide Agents

In some embodiments, an active agent is a peptide. Suitable peptides include peptides of from about 3 amino acids to about 50 amino acids, from about 5 amino acids to about 30 amino acids, from about 10 amino acids to about 25 amino acids, from about 25 amino acids to about 50 amino acids, from about 50 amino acids to about 75 amino acids, or from about 75 amino acids to about 100 amino acids in length.

In some embodiments, the peptide is linear; in other embodiments, the peptide is cyclized. In some embodiments, the peptide is modified, e.g., comprises one or more non-peptide moieties covalently or non-covalently linked to the peptide. Suitable non-peptide moieties include, but are not limited to, polyethylene glycol (PEG) moieties; carbohydrate moieties; lipid moieties; fatty acid moieties; polysaccharide moieties; phosphate groups; and the like. In some embodiments, the active peptide is linked to a heterologous peptide, e.g., a heterologous peptide that confers increased stability or residence time in vivo; a heterologous peptide that facilitates crossing a cell membrane; a heterologous peptide that binds to a cell surface receptor; a heterologous peptide that provides for dimerization; a heterologous peptide that provides an epitope tag; a heterologous peptide that provides a detectable signal; and the like.

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A peptide may be a depsipeptide, which may be a linear or a cyclic depsipeptide. Kuisle et al. (1999) Tet. Letters 40; 1203-1206. "Depsipeptides" are compounds containing a sequence of at least two alpha-amino acids and at least one alpha-hydroxy carboxylic acid, which are bound through at least one normal peptide link- and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

Peptides may be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide EMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art.

The term "bicyclic" refers to a peptide in which there exists two ring closures. The ring closures are formed by covalent linkages between ammo acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at the terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, a peptide or peptidomimetic can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. Nos. 4,640,835; 4,496,689; 4,301,144; 4,670,417; 4,791,192; 4,179,337 or WO 95/34326.

An active peptide will in some embodiments be conjugated to decapeptides comprised of Arginine residues to allow uptake across the plasma membrane by protein transduction. Such modifications allow peptides to enter cells (e.g., cross the plasma membrane) with high efficiency.

In some embodiments, an active peptide is a peptide aptamer. Peptide aptamers are peptides or small polypeptides that act as dominant inhibitors of protein function. Peptide aptamers specifically bind to target proteins, blocking their function ability. Kolonin and Finley (1998) *Proc. Natl. Acad. Sci. USA* 95:14266-14271. Due to the highly selective nature of peptide aptamers, they may be used not only to target a specific protein, but also to target specific functions of a given protein (e.g. a protein binding function). Further, peptide aptamers may be expressed in a controlled fashion by use of promoters which regulate expression in a temporal, spatial or inducible manner.

Peptide aptamers that bind with high affinity and specificity to a target protein may be isolated by a variety of techniques known in the art. Peptide aptamers can be isolated from random peptide libraries by yeast two-hybrid screens (Xu et al, (1997) *Proc. Natl. Acad. Sci. USA* 94:12473-12478). They can also be isolated from phage libraries (Hoogenboom et al, *Immunotechnology* (1998) 4:1-20) or chemically generated peptides/libraries.

Dosages

The amount of subject agent which is administered will vary with the nature of the agent. As one non-limiting example, a subject agent can be administered in the range of about 0.2 mg/kg/day to about 20 mg/kg/day. The determination of how large a dose is to be used may be determined using an animal model (e.g., a non-human primate model) and relating the dosage based on pharmacokinetics, e.g. with equations predictive of interspecies scaling. Usually, the lowest effective dose will be used.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six-months, one year, or two years, or more, depending on various factors.

Formulations

An active agent is administered to an individual in need thereof in a formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Routes of Administration

Conventional and pharmaceutically acceptable routes of administration include intranasal, intramuscular, intratracheal, intratumoral, transdermal, subcutaneous, intradermal, topical application, intravenous, vaginal, nasal, and other parenteral routes of administration. Suitable routes of administration also include oral and rectal routes. Routes of administration may be combined, if desired, or adjusted depending upon the agent and/or the desired effect. The composition can be administered in a single dose or in multiple doses.

Parenteral routes of administration other than inhalation administration include, but are not necessarily limited to, topical, vaginal, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Combination Therapies

A subject agent can be administered to an individual in combination (e.g., in the same formulation or in separate formulations) with at least a second therapeutic agent ("combination therapy"). The subject agent can be administered in admixture with a second therapeutic agent or can be administered in a separate formulation. When administered in separate formulations, a subject agent and a second therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a therapeutic agent are as described above.

Dosages, Routes of Administration, and Formulations

As mentioned above, an effective amount of the active agent is administered to the host, where "effective amount" means a dosage sufficient to produce a desired result. Generally, the desired result is at least a reduction in the level of active HDAC8 in a smooth muscle cell as compared to a control.

In the subject methods, the active agent(s) may be administered to the host using any convenient means capable of resulting in the desired reduction in the level of active HDAC8 in a smooth muscle cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the therapeutic DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Subjects Suitable for Treatment

Subjects suitable for treatment with a subject treatment method include any individual who has been diagnosed as having a smooth muscle disorder. Subjects suitable for treatment with a subject treatment method also include individuals who have a smooth muscle disorder, and who have been treated with an agent to treat the disorder, but who either no longer respond to such treatment, or in whom such treatment is otherwise contraindicated.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Expression of HDAC8 in Cells Showing Smooth Muscle Differentiation in Normal Human Tissues Materials and Methods
Cell Lines, Tissue Culture, and Reagents NIH-3T3 mouse embryonic fibroblast and HeLa human cervix epithelial cell lines were purchased from the American Type Culture Collection (Manassas, Va., USA). Primary human skin fibroblasts were established by outgrowth of normal human skin biopsies as detailed elsewhere. Delvoye et al. (1983) *J. Invest. Dermatol.* 81:267-270; and Deroanne et al. (2002) *Oncogene* 21:427-436. Primary human smooth muscle cells (HSMC) were harvested from human umbilical cord veins, essentially as previously described (Deroanne et al., supra; and Deroanne et al. (2003) *J. Cell. Sci.* 116:1367-1376) after removal of the endothelial cell layer. Jaffe et al. (1973) *J Clin. Invest.* 52:2745-2756. Briefly, umbilical cord veins were cannulated and flushed with 50 mL RPMI 1640 culture medium (Invitrogen, Merelbeke, Belgium) to remove blood, and allowed to drain. The vein was then filled with 1 mg/mL collagenase A (Roche) in RPMI 1640 and incubated at 37° C. in a bath containing sterile DPBS (Dulbecco's PBS w/o calcium, magnesium, and sodium bicarbonate) for 10 minutes. Endothelial cells were removed by thoroughly flushing with 50 ml RPMI 1640. The vein was further rinsed with 50 ml RPMI 1640 prior to reintroducing collagenase A in its lumen. After incubation at 37° C. for 20 minutes, smooth muscle cells were harvested by thoroughly flushing with 50 mL RPMI 1640, centrifuged, resuspended in culture medium, and seeded onto Petri dishes. All cells were grown and maintained in Dulbecco's modified Eagle's medium (DMEM) supplemented with 10% decomplemented (heat-inactivated) fetal bovine serum (FBS, Biowhittaker), 50 U/mL penicillin, 50 μg/mL streptomycin, 0.1% fungizone and 2 mM L-glutamine at 37° C. in a humidified 95% air/5% $CO_2$ atmosphere. Primary human cells were used between passages 7 and 13. In vitro grown HSMCs displayed a typical smooth muscle cell morphology and immunoblot experiments enabled to check that, at passages 7 through 13, HSMCs retained α-SMA and smooth muscle myosin heavy chain (SMMHC) expression. All tissue culture reagents were obtained from nitrogen (Merelbeke, Belgium) unless otherwise specified.

Tissues

Formalin-fixed paraffin-embedded normal human tissue samples were obtained from the Department of Pathology at the University Hospital of Liège, Belgium. The organs from which the tissues were sampled are listed in Table 1, below.

Cloning of HDAC8, Transfections, and Immunofluorescence

Total RNA was extracted from HSMCs using the RNeasy mini kit (Qiagen, Inc., Valencia, Calif.), according to the manufacturer's protocol. To obtain the full length human HDAC8 cDNA, an RT-PCR amplification of HSMC total RNA was set up with the use of the Pfu DNA polymerase (Promega, Leiden, The Netherlands) and the following primers: 5'-CACCATGGACGAGCCGGAGGAA-3' (GenBank NM_018486 bases 43-60; SEQ ID NO:2) and 5'-GACCACATGCTTCAGATTCCCTT-3' (GenBank NM_018486; complementary to bases 1173-1149; SEQ ID NO:3). pcDNA3.1D/HDAC8/V5-His was constructed by directional cloning of the HDAC8 coding sequence upstream of and in-frame with the carboxyl-terminal V5 epitope and hexahistidine sequence into pcDNA3.1D/V5-His-Topo® (Invitrogen, Merelbeke, Belgium). Mock transfection with transfecting reagent alone and transfection with pcDNA3.1D/lacZ/V5-His plasmid (Invitrogen, Merelbeke, Belgium) served as controls. The HDAC8 construct was checked by DNA sequencing of the insert and multiple cloning sites. Human HDAC3, HDAC6 and HDAC8 cDNAs were also subcloned to generate C-terminal FLAG-tagged fusions into a FLAG vector (a derivative of the pcDNA3.1(+) vector backbone (Invitrogen)), as previously described. Fischle et al. (1999) *J. Biol. Chem.* 274:11713-11720; and North et al. (2003) *Mol. Cell.* 11:437-444.

NIH-3T3 cells grown on coverslips in 35-mm dishes were transfected at a density of $3 \times 10^4$ cells/$cm^2$ with 2 μg of pcDNA3.1D/HDAC8/V5-His or pcDNA3.1D/lacZ/V5-His plasmid and 6 μl of FUGENE 6™ transfection reagent (Roche Applied Science, Indianapolis, Ind.), according to the manufacturer's directions. Cells were cultured for 24 h, washed twice with PBS (10 mM sodium phosphate and 0.9% NaCl [pH 7.4]), and either fixed with 2% formaldehyde for 15 min or subjected to lysis for total protein extraction. Detection of V5-tagged proteins was performed by Western blot analysis, as detailed below. Indirect immunofluorescence was used to show the sub-cellular localization of V5-tagged HDAC8. Briefly, after fixation and 2 washes in PBS, the endogenous peroxidase activity was blocked with 0.3% hydrogen peroxide in methanol for 30 min. Following washes in distilled water for 5 min and in PBS for 20 min, cells were permeabilized with 0.2% Triton-X-100 (Sigma Chemical Co., St Louis, Mo., USA) for 5 min on ice. The slides were then incubated with 3% normal horse serum (NHS) (Vector Lab. Inc., Burlingame, Calif., USA) in PBS for 30 min to block the non-specific serum-binding sites. Anti-V5 antibody (Invitrogen, Merelbeke, Belgium) at a dilution of 1:500 was applied and incubated for 1 hr, followed by incubation with a biotinylated horse anti-mouse IgG antibody and the avidin-biotin-peroxidase complex ABC (Vectastain Elite immunoperoxidase kit, Vector Laboratories, Inc., Burlingame, Calif., USA).

After each incubation, the slides were washed 3 times with 1% NHS in PBS for 5 min. Peroxidase activity was developed with a solution containing fluorescein isothiocyanate (FITC)-conjugated tyramine in amplification diluent NEN, Boston, Mass., USA). After 3 washes in PBS for 10 min, the cells were counterstained with 4',6'-diamidino-2'-phenylindole dichloride (DAPI, Roche Diagnostics) and the coverslips were mounted with antifading fluorescent mounting medium (DAKO, Carpinteria, Calif., USA) for microscopic examination. Color photomicrographs of the slides were taken with an Axioplan fluorescence microscope (Zeiss) equipped with appropriate filter sets.

For double immunofluorescence staining experiments, NIH-3T3 cells grown on coverslips were transfected with pcDNA3.1(+)/HDAC3/FLAG, pcDNA3.1(+)/HDAC6/FLAG or pcDNA3.1(+)/HDAC8/FLAG and FUGENE 6™ transfection reagent. NIH-3T3 cells transfected with pcDNA3.1(+)/FLAG alone served as negative control. Transfected cells were processed for immunofluorescence microscopy 48 hours after transfection. Cells on coverslips were washed twice in PBS for 10 min, fixed in 4% paraformaldehyde for 10 min, followed by permeabilization in 0.5% Triton-X-100 in PBS for 10 min. After three washes for 10 min each in PBS, cells were incubated for 10 min in 10% BSA in PBS and then incubated for 1 hr with anti-α-SMA or anti-FLAG antibodies or together, each diluted 1:500 in PBS+0.1% Tween-20. Cells were washed three times 10 min in PBS containing 0.1% Tween-20, followed by incubation for 1 hr with donkey anti-mouse IgG Cy2-conjugated or donkey anti-rabbit IgG Cy3-conjugated secondary antibodies (Jackson ImmunoResearch Laboratories, Inc. West Grove, Pa.) or together, each diluted 1:500 in PBS+0.1% Tween-20. Cells were then washed three times for 10 min each in PBS and once briefly in ddH$_2$O, and mounted on slides with Gel Mount (Biomeda Corp., Foster City, Calif.). Confocal images were acquired by laser-scanning confocal microscopy with an Olympus BX60 microscope equipped with a Radiance 2000 confocal setup (Bio-Rad).

Antibodies

Anti-HDAC8 antibody (N-20) was raised against an epitope mapping at the N-terminus of human HDAC8 (Santa Cruz Biotech., Inc, Santa Cruz, Calif., USA). Polyclonal rabbit anti-HDAC1 (#2062), anti-HDAC3 (#2632) and anti-HDAC5 (#2082) antibodies were purchased from Cell Signaling Technology (Beverly, Mass., USA). Anti-α-tubulin (clone B512), anti-α-SMA (clone 144), and anti-SMMHC (M-7786) monoclonal antibodies as well as anti-FLAG (F-7425) rabbit polyclonal antibody were from Sigma (Bornem, Belgium).

Protein Extraction

HDAC8 protein expression was examined in primary HSMCs and fibroblasts and in HeLa epithelial cells. After rinses in PBS (PBS Dulbecco's without calcium, magnesium, and sodium bicarbonate), in vitro grown subconfluent cells were scrapped and pelleted by centrifugation at 300×g for 10 min. Total protein lysates were obtained by incubating cell pellets with protein lysis buffer containing 0.1% Triton X-100, 500 mM Tris (pH 7.5), 250 mM NaCl, 1 mM EDTA, 1 mM dithiothreitol (DTT), 1 mM phenylmethylsulfonyl fluoride and Complete® protease inhibitor cocktail (Roche). Protein lysates were placed in ice for 30 rain, vortexed every 10 min, and then cleared by centrifugation at 12,000×g for 20 min at 4° C. The supernatants were retrieved and frozen at 80° C. until use in immunoblot assays. The protein concentration was measured using a bicinchoninic acid determination kit (Pierce Chemical Co., Rockford, Ill., USA).

Immunoblotting

Equal amounts of protein lysates were resolved by size on 10% Bis-Tris-polyacrylamide gels (Invitrogen, Merelbeke, Belgium) and transferred onto polyvinylidene difluoride membranes (Roche Diagnostics, Mannheim, Germany), which were stained with Ponceau S (Sigma Chemical Company, St. Louis, Mo.) to examine the equal protein sample loading and transferring. The membranes were blocked with 5% non-fat dry milk in Tris-buffered saline (20 mM Tris base [pH 7.6], 150 mM NaCl) containing 0.1% Tween-20 (TBS-T), and probed with the following primary antibodies: anti-HDAC1, anti-HDAC3, anti-HDAC8, and anti-α-tubulin. After washing in TBS-T, membranes were incubated with horseradish peroxidase (HRP)-conjugated secondary antibodies (Bio-Rad Laboratories, Hercules, Calif.) and developed using an enhanced chemiluminescence detection system (ECL detection kit; Amersham Corp., Arlington Heights, Ill.), according to the instructions of the manufacturer. Membranes were exposed to Kodak X-Omat AR films.

Nuclear and Cytoplasmic Fractionation

Approximately $10^7$ cells were collected and washed twice in ice-cold PBS. The cell pellet was resuspended in 1 mL of washing buffer (10 mM Hepes, pH 7.9, 20 mM KCl, 2 mM MgCl$_2$, 0.1 mM EDTA, 1 mM DTT, and protease inhibitors), microcentrifuged at 100×g for 2 min at 4° C., and then lysed in 500 µl of buffer A (10 mM Hepes, pH 7.9, 10 mM KCl, 2 mM MgCl$_2$, 0.1 mM EDTA, 0.2% Nonidet P-40, 1 mM DTT, and protease inhibitors). After incubation on ice for 30 sec, nuclei were pelleted by microcentrifugation at 3500×g for 5 min at 4° C. and supernatant was collected as the cytoplasmic fraction. The nuclei pellet was washed 3 times in 500 µl of washing buffer and then resuspended in one volume of buffer B (20 nM Hepes, pH 7.9, 630 mM NaCl, 1.5 mM MgCl$_2$, 25% glycerol, 0.2 mM EDTA, 0.5 mM DTT and protease inhibitors). The suspension was mixed gently by rocking for 45 min at 4° C. and then centrifuged at 14,000×g for 30 min at 4° C. Supernatant was collected as the nuclear fraction. The amount of HDAC1, HDAC3, HDAC8, and α-tubulin in the fractionated nuclear and cytoplasmic cell extracts was analyzed by immunoblotting, as detailed above.

Immunoperoxidase

Detection of HDAC8 protein in human tissues and cells was performed with the use of an immunoperoxidase technique and the ABC Vectastain Elite kit (Vector Laboratories, Inc., Burlingame, Calif., USA) according to the supplier's directions with some modifications. Primary human skin fibroblasts, murine NIH-3T3 fibroblasts, and HSMCs were seeded onto poly-L-lysine-coated glass slides, grown to 70%-80% confluence, washed with PBS, and then fixed with freshly prepared 2% formaldehyde for 15 min. Five µm formalin-fixed paraffin-embedded tissue sections were deparaffinized in xylene and rehydrated in graded alcohols. After blocking of the endogenous peroxidase activity with 0.3% hydrogen peroxide in methanol for 30 min, the sections were heated in a water-bath at 95° C. in citrate buffer, allowed to cool down, and then incubated with 1% normal horse serum (α-SMA and SMMHC), 1% normal goat serum (HDAC5) or 1% normal swine serum (HDAC8) in PBS for 30 min, For anti-SMMHC immunostaining, an additional trypsinization step was carried out as previously described (Longtine et al. (1985) *J. Histochem. Cytochem.* 33:179-184) before heating the sections for antigen retrieval; tissue sections were incubated with 0.125 mg/ml trypsin (Gibco) in PBS for 20 min at 37° C. and then washed with PBS for 20 min. Mouse anti-α-SMA antibody at a dilution of 1:400, mouse anti-SMMHC antibody at a dilution of 1:2500, rabbit anti-HTDAC5 antibody at a dilution of 1:500 or goat anti-HDAC8 antibody at a dilution of 1:200 was incubated overnight at 4° C., followed by biotinylated horse anti-mouse, goat anti-rabbit or swine anti-goat IgG antibody and the avidin-biotin-peroxidase complex. Washes were performed 3 times with PBS after each incubation step.

Peroxidase activity was developed by a solution of 3-3' diaminobenzidine tetrahydrochloride (DAB) (Vel, Leuven, Belgium) dissolved in PBS and 0.03% $H_2O_2$. The DAB solution was filtered and applied to the sections for 4 min. Finally, Carazzi's hematoxylin was used to counterstain the slides that were then dehydrated and mounted. Control experiments included omission of the first antibody and preincubation of anti-HDAC8 antibody with a 50 molar excess of the corresponding peptide prior to the antibody's use in the immunoperoxidase assay. Masson's trichrome staining was carried out on paraffin-embedded tissues as previously described (Hallahan et al. (2002) *J. Natl. Cancer Inst.* 94:733-741) to delineate collagen and smooth muscle fibers. Photomicrographs of the slides were taken with a Zeiss microscope.

Results

HDAC8 Expression in Normal Human Tissues is Restricted to Cells Showing Smooth Muscle Differentiation Immunohistochemistry was performed with the use of a specific anti-HDAC8 antibody to assess HDAC8 expression in a large number of normal human tissue types and organs. Masson's trichrome staining was used to distinguish collagen and smooth muscle fibers present in the wall of small arteries. Anti-HDAC8 immunoreactivity was detected only in the smooth muscle cells of the vascular walls. Control immunohistohemical experiments in which the anti-HDAC8 antibody had been preincubated with a molar excess of the corresponding peptide completely abolished the labeling. Similarly, no specific staining was observed when the primary antibody was replaced with PBS in the immunoperoxidase procedure.

Anti-HDAC8 immunoreactivity, characterized by intense diffuse cytoplasmic staining, was exclusively detected in vivo in human cells showing smooth muscle differentiation, in extenso visceral and vascular smooth muscle cells, myoepithelial cells, and myofibroblasts. Table 1 details the distribution of HDAC8 expression in the various human tissues analyzed.

TABLE 1

Localization of HDAC8 expression in various normal human tissues and organs.

| Anatomical structure | Distribution of HDAC8 expression |
|---|---|
| Respiratory tract | |
| Trachea, bronchi and bronchioli | Myoepithelial cells from mucous glands# Muscular layer° |
| Lung | Alveolar septae myofibroblasts* |
| Genitourinary tract | |
| Kidney | Muscular layer of renal pelvis° Capsule° |
| Ureter | Muscular layer° |
| Urinary bladder | Muscular layer° |
| Prostate | Stromal cells* |
| Vas deferens and epididymis | Periductal layer° |
| Testis | Peritubular myoid cells* |
| Uterus | Myometrium° Cervix stroma° |
| Fallopian tube | Muscular layer° |
| Ovary | External theca cells* |
| Gastrointestinal tract | |
| Small intestine and colon | Muscularis mucosae° Muscularis propria° Subepithelial myofibroblasts in lamina propria* |
| Stomach | NA |
| Esophagus | NA |
| Gallbladder | NA |
| Pancreas | NR |
| Liver | Capsule° |
| Lymphoid organs | |
| Spleen | Capsule° Reticular cells* |
| Thymus | NR |
| Endocrine glands | |
| Salivary glands | Myoepithelial cells# |
| Thyroid and parathyroid glands | NR |
| Adrenal gland | Capsule° |
| Nervous system | |
| Spinal cord | NR |
| Peripheral nerve | NR |
| Brain | NR |
| Muscles | |
| Myocardium | NR |
| Skeletal muscle | NR |
| Other tissues and organs | |
| Bone | NR |
| Skin | Erector pili° Myoepithelial cells of sweat glands# |
| Mammary gland | Myoepithelial cells of lobules and ducts# |

NA: not assessed;
NR: no specific reactivity, with the exception of vascular reactivity that was detected in smooth muscle cells from arteries, arterioles, veins, and venules as well as in pericytes from all organs and tissues tested
°smooth muscle cells;
myoepithelial cells;
*myofibroblasts HDAC8 expression was detected in vascular smooth muscle cells, including large vessel (arteries and veins) and microvessel (arterioles, venules, and capillaries) smooth muscle cells. Anti-HDAC8 immunoreactivity was also found in smooth muscle cells from all smooth muscle-containing organs tested, such as intestine, lung, fallopian tubes, and bladder.

HDAC8 expression was also searched in myoepithelium-bearing glands, including mammary gland alveoli and ducts, respiratory tract mucous glands, salivary glands, and skin eccrine glands. HDAC8 was detected in myoepithelial cells from all these glandular structures. To assess the possible co-localization of HDAC8 with smooth muscle α-actin (α-SMA) and smooth muscle myosin heavy chain (SM-MHC), 2 well-known smooth muscle-specific cytoskeleton proteins, serial sections from normal human breast, trachea, salivary glands, and skin tissues were subjected to immunohistochemistry using specific anti-HDAC8, anti-α-SMA, and anti-SMMHC antibodies. The results showed that myoepithelial cells from mammary acini/ducts, tracheal mucous glands, salivary glands, and skin eccrine glands co-expressed the 3 proteins.

HDAC8 expression was also detected in various myofibroblasts-containing tissues. HDAC8 expression was found in smooth muscle cells from vascular walls, in smooth muscle cells from muscularis mucosae, as well as in intestinal subepithelial myofibroblasts present in the lamina propria and extending from the muscularis mucosae to the subepithelial aspect of the surface epithelium. In testis, HDAC8 expression was observed in a thin layer of myofibroblasts peritubular myoid cells) located around seminiferous tubules. Myofibroblastic cells from several, but not all, other myofibroblasts-containing normal human tissues analyzed also exhibited HDAC8 expression. Indeed, in addition to its detection in testis peritubular myoid cells and intestine subepithelial myofibroblasts, HDAC8 was also expressed by lung alveolar septae myofibroblasts, prostate stromal cells, reticular cells of the spleen, and external theca cells of the ovary. Interestingly, like myoepithelial cells, all these myofibroblastic cells co-expressed HDAC8, α-SMA, and SMMHC. No specific anti-HDAC8 immunoreactivity was detected in some other types of myofibroblastic cells, such as reticular cells of the thymus, stromal cells of the breast, periacinar stellate cells of the pancreas, perisinusoidal stellate (Ito) cells of the liver, and mesangial cells of the kidney.

HDAC8 protein was not detected in non-smooth muscle cells. In particular, striated muscle, neuronal, endothelial, and epithelial cells as well as osteocytes, chondrocytes, lymphocytes, and fibrocytes were devoid of anti-HDAC8 immunoreactivity.

Figure 1:
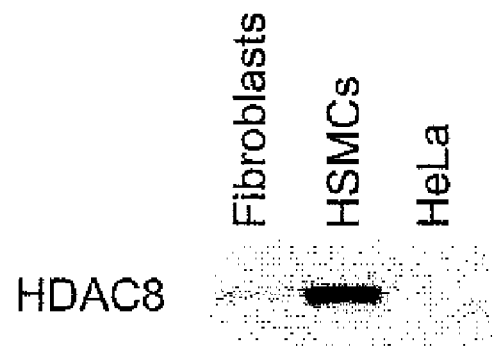
FIG. 1 depicts immunoblot analysis of HDAC8 in protein lysates from primary human skin fibroblasts, primary human smooth muscle cells (HSMCs), and HeLa human cervix epithelial cells.

HDAC8 expression was also investigated by immunoblot in in vitro grown human smooth muscle cells (HSMCs), human skin fibroblasts, and human HeLa cervix epithelial cells. Among the 3 cell lines, the abundance of HDAC8 was the highest in HSMCs, with lower levels in human fibroblasts, as shown in FIG. 1. As discussed above, it had observed that cervix keratinocytes from normal human tissues did not express detectable levels of HDAC8. Similarly in vitro grown HeLa human cervix epithelial cells exhibited no detectable expression of the enzyme (FIG. 1).

FIG. 1. Protein lysates from primary human skin fibroblasts, primary human smooth muscle cells (HSMCs), and HeLa human cervix epithelial cells were subjected to immunoblot analysis of HDAC8 expression, as described in Materials and Methods. HDAC8 expression was investigated in human primary skin fibroblasts and smooth muscle cells from human umbilical cord vein (HSMC), by immunoperoxidase, as described in Materials and Methods. Anti-HDAC8 immunostaining presented a pattern suggestive of a cytoskeletal association in HSMCs.

HDAC8 is a Predominantly Cytoplasmic HDAC and Co-Localizes with α-SMA

In all human tissues in which HDAC8 expression was detectable, the enzyme was present mainly in the cytoplasmic compartment of the enzyme-expressing cells. This contrasted with the sub-cellular localization of HDAC5, a class II HDAC involved in skeletal muscle differentiation. Indeed, HDAC5 expression was observed in the nucleus of cardiac myocytes.

Immunocytochemistry experiments also showed the prominent cytoplasm localization of HDAC8 in HSMCs, with a distribution pattern suggestive of a cytoskeletal association. In order to verify the specificity of the anti-HDAC8 immunoreactivity obtained in primary cultures, the antibody was preincubated with a molar excess of the corresponding peptide. The preincubation of the antibody with its peptide produced a complete disappearance of the staining. Similarly to fibroblasts in human tissues, cultured fibroblasts usually exhibited no detectable expression of HDAC8. Murine NIH-3T3 fibroblasts displayed both nuclear and cytoplasmic expression of HDAC8. The cytoplasmic distribution of HDAC8 in these cells was similar to that observed in HSMCs.

To further examine the sub-cellular localization of HDAC8, we performed cell fractionation experiments with the use of primary human fibroblasts, HSMCs, and NIH-3T3 cells. After separation of the cytoplasm and nuclear fractions, HDAC8 was enriched in the cytoplasm fraction, while HDAC1 and the cytoskeleton protein α-tubulin were localized exclusively in the nucleus and in the cytosol, respectively. HDAC3 was mainly localized in the nuclear compartment although it was also detected in the cytosol (FIG. 2).

Figure 2:
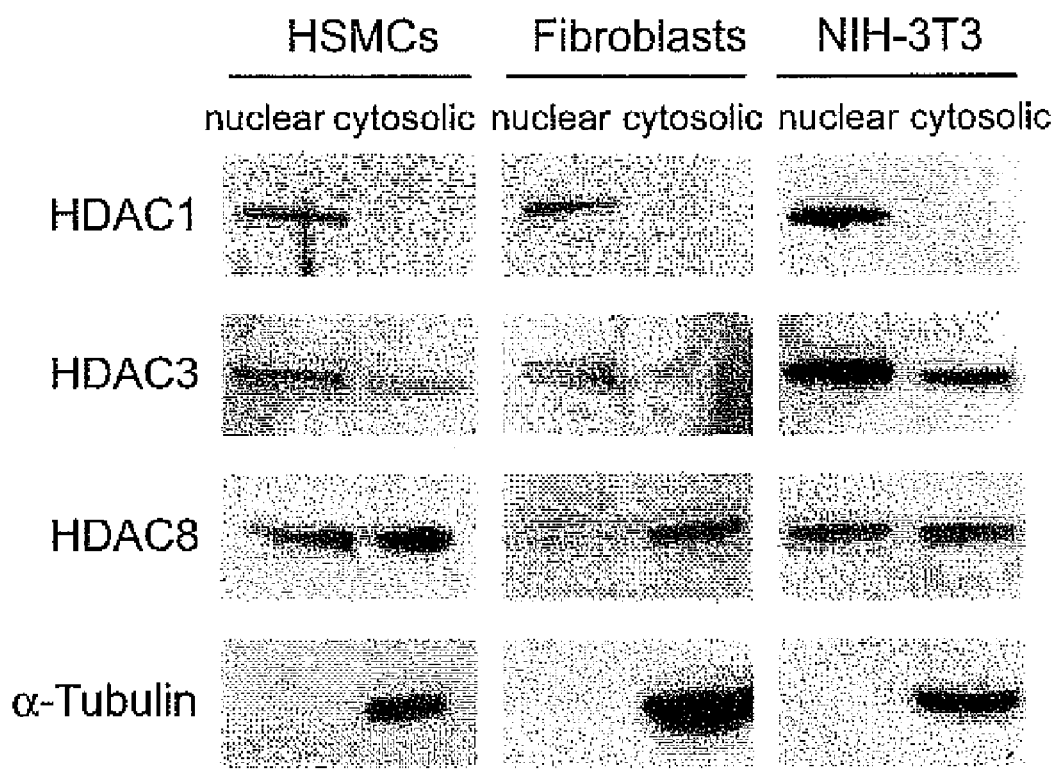
FIG. 2 depicts immunoblot analysis of HDAC1, HDAC3, HDAC8, and α-tubulin in fractionated nuclear and cytosolic extracts from primary human skin fibroblasts, HSMCs, and NIH-3T3 fibroblasts.

FIG. 2. The amount of HDAC1, HDAC3, HDAC8, and α-tubulin in the fractionated nuclear and cytosolic extracts from primary human skin fibroblasts, HSMCs, and NTH-3T3 fibroblasts was analyzed by immunoblotting, as described in Materials and Methods.

Figure 3:
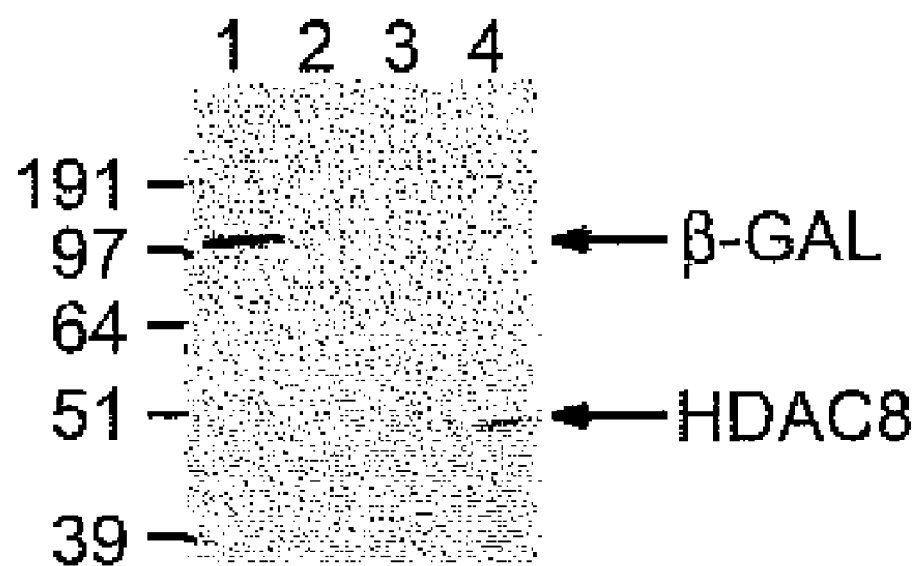
FIG. 3 depicts Western blot analysis of transfected recombinant human HDAC8 in NIH-3T3 cells.

Transfection experiments also indicated that HDAC8 could be localized in the cytoplasm. A V5-tagged HDAC8 construct was transiently transfected into NIH-3T3 cells. Forced expression of the tagged enzyme was checked by immunoblot analysis using an anti-V5 antibody (FIG. 3). Indirect immunofluorescence using the same antibody was used to visualize the cellular localization of transfected HDAC8. Exogenous HDAC8 was localized both in the cytoplasm and in the nucleus of NIH-3T3 cells.

FIG. 3. Western blot analysis of transfected recombinant human HDAC8 in NIH-3T3 cells. Total cell extracts from NIH-3T3 cells transiently transfected with pcDNA3.1D/HDAC8/V5-His, as in Materials and Methods, were subjected to immunoblot analysis using an anti-V5 antibody (Invitrogen). Lane designations were as follows: lane 1, NIH-3T3 transiently transfected with pcDNA3.11D/lacZ/V5-His, lane 2 NIH-3T3 transiently transfected with the insert-less vector, lane 3, untranfected NIH-3T3 cells, lane 4, NIH-3T3 transiently transfected with pcDNA3.1D/HDAC8/V5-His.

In cultured HSMCs and NIH-3T3 cells, the distribution of HDAC8 expression was reminiscent of stress fibers-like structures, suggesting a possible association of the enzyme with the smooth muscle cytoskeleton. In order to investigate whether HDAC8 may associate with smooth muscle cytoskeleton proteins, and in particular with α-SMA, double immunofluorescence staining experiments coupled with confocal microscopy analysis were carded out with an antibody for α-SMA on one hand, and with an anti-FLAG antiserum after transfection of cDNAs encoding either HDAC3, HDAC6 or HDAC8 (C-terminal FLAG-tagged) in NIH-3T3 cells. Exogenous HDAC8, detected with an anti-FLAG antibody, was present in the nuclear and cytoplasmic compartments. Thus, exogenously expressed HDAC8 displayed an intra-cellular localization similar to that of endogenously expressed HDAC8. In the cytoplasm, FLAG-tagged HDAC8 displayed a stress fibers-like distribution of expression, and more importantly, co-localized with α-SMA, mainly as filamentous structures. No co-localization was found between α-SMA and either FLAG-tagged HDAC3, which was almost exclusively nuclear, or FLAG-tagged HDAC6, which is known to associate with α-tubulin.

Example 2

Histone Deacetylase HDAC8 Associates with Smooth Muscle α-Actin and Regulates Smooth Muscle Contractility Materials and Methods
Cell Lines, Tissue Culture, and Reagents NIH-3T3 mouse embryonic fibroblast cell line (ATCC CRL-1658) was purchased from the American Type Culture Collection (Manassas, Va., USA). Primary human vascular smooth muscle cells (HSMC) were isolated from human umbilical cord vein, and primary human skin fibroblasts were established by outgrowth of normal human skin biopsies as detailed elsewhere (Delvoye et al. (1983) supra; and Deroanne et al. (2002) supra). All cells were maintained in Dubelcco's modified Eagle's medium (DMEM) supplemented with 10% decomplemented (heat-inactivated) fetal bovine serum (FBS, ICN) and 2 mM L-glutamine at 37° C. in a humidified 95% air/5% $CO_2$ atmosphere. Primary human cells were used between passages 9 and 14. All tissue culture reagents were obtained from Invitrogen (Merelbeke, Belgium) unless otherwise specified.

Tissues

Fresh non cancerous prostate tissue samples were obtained from patients who had undergone a radical prostatectomy for clinically localized prostate cancer in the Department of Urology at the University Hospital of Liège, Belgium. Snap-frozen normal prostate tissues were harvested from radical prostatectomy specimens as previously described. Wheeler et al. (1994) *Prostate* 25:274-279; and van den Brute et al. (2001) *J. Pathol.* 193:80-87. The Ethics Committee of the University Hospital of Liège approved the specific protocol used in this study.

Protein Extraction

Cells were rinsed and scrapped in phosphate-buffered saline (Dulbecco's PBS minus divalent cations) and then pelleted by centrifugation at 1600×g for 10 minutes. Pulverization of the snap-frozen prostate tissues was performed with the use of a Mikro-Dismembrator U (Braun Biotech., Melsungen, Germany) and generated tissue powder that was immediately processed for protein extraction. Total protein lysates were obtained by incubating cell pellets or tissue powder with protein lysis buffer (0.1% Triton X-100, 50 mM Tris (pH 7.5), 250 mM NaCl, 1 mM EDTA, 50 mM NaF, 1 mM $Na_3VO_4$, 1 mM dithiothreitol) containing 1 mM phenylmethylsulfonyl fluoride (PMSF) and Complete protease inhibitor cocktail (Roche). Protein lysates were placed in ice for 30 min, vortexed every 10 min, and then cleared by centrifugation at 12,000×g for 20 min at 4° C. The supernatants were retrieved and frozen at −80° C. until use in immunoblot assays. The protein concentration was measured using a bicinchoninic acid (BCA) determination kit (Pierce Chemical Co., Rockford, Ill., USA).

Antibodies

Anti-HDAC8 antibodies (N-20, E-5) were obtained from Santa Cruz Biotech., Inc. (Santa Cruz, Calif., USA). Polyclonal rabbit anti-HDAC1 (#2062) and anti-HDAC3 (#2632) antibodies were purchased from Cell Signaling Technology (Beverly, Mass., USA). Anti-α-tubulin (clone B-5-1-2), anti-acetylated α-tubulin (clone 6-11B-1), anti-smooth muscle myosin heavy chain (SMMHC) (clone HSM-V) and anti-β-actin (clone AC-15) monoclonal antibodies were from Sigma-Aldrich (Bornem, Belgium). Anti-smooth muscle α-actin (clone 1A4) antibody, IgG1 (clone DAK-GO1), and IgG2a (clone DAK-GO5) were obtained from Dako (Glostrup, Denmark). Goat anti-rabbit IgG, rabbit anti-mouse IgG and donkey anti-goat IgG horseradish peroxidase (HRP)-conjugated secondary antibodies were purchased from Bio-Rad Laboratories (Hercules, Calif., USA), Dako (Glostrup, Denmark) and Santa Cruz Biotech., Inc. (Santa Cruz, Calif., USA) respectively.

Western Blotting

Protein lysates were resolved by size on NuPAGE® Bis-Tris or SDS-polyacrylamide gels (Invitrogen and Bio-Rad) and transferred, as recommended by the manufacturers, onto polyvinylidene difluoride (Roche Diagnostics, Mannheim, Germany) or nitrocellulose (Bio-Rad, Hercules, Calif.) membranes, which were stained with Ponceau S (Sigma Chemical Company, St. Louis, Mo.) to examine the equal protein sample loading and transferring. The membranes were blocked with 5% non-fat dry milk in Tris-buffered saline (20 mM Tris base [pH 7.6], 150 mM NaCl) containing 0.1% Tween-20 (TBS-T), and probed with primary antibodies. After washing in TBS-T, membranes were incubated with horseradish peroxidase (HRP)-conjugated secondary antibodies and developed using an enhanced chemiluminescence detection system (ECL detection kit; Amersham Corp., Arlington Heights, Ill.) according to the instructions of the manufacturer. Membranes were exposed to Kodak X-Omat AR films.

Co-Immunoprecipitation Assays

Protein lysates from HSMCs and from human prostate tissues were subjected to immunoprecipitation using anti-α-SMA, anti-β-actin or anti-SMMHC mouse monoclonal antibodies to study the potential association of these cytoskeletal proteins with HDAC8. Pelleted cells and prostate tissue powder were lysed either in ice cold low stringency buffer (containing 0.5% Triton X-100, 50 mM Tris-HCl [pH 8.0] in physiological solution) or in high stringency buffer (containing 0.5% Triton X-100, 50 mM Tris-HCl [pH 8.0], 0.1% SDS, 0.5% sodium deoxycholate (DOC) in physiological solution), as previously described. Durst et al. (1979) *Mol Cell Biol.* 23:607-619. Protease inhibitors (50 mM NaF, 2 mM $Na_3VO_4$, 1 mM PMSF, and Complete®, protease inhibitors mixture from Roche) were added freshly. Protein lysates were incubated at 4° C. for 30 minutes, vortexed every 10 minutes and then centrifuged at 12,000×g for 20 minutes at 4° C. Protein extracts were precleared by incubation with 150 µl of a 50% slurry of protein G-sepharose beads (Amersham Biosciences) for 2 hours at 4° C. on orbital shaker.

Equal amounts of total protein extracts (1500 µg per immunoprecipitation), as determined by BCA Protein Assay (Pierce Chemical Co., Rockford, Ill., USA), were incubated with anti-(α-SMA, anti-β-actin or anti-SMC antibody into the corresponding lysis buffer overnight at 4° C. with constant rotation. Control samples were incubated with the same concentration of non-immune mouse IgG2a (a-SMA and β-actin) or IgG1 (SMMHC). Subsequently, 75 µl of a 50% slurry of protein G sepharose beads were added to each sample and incubated for 1 hr at 4° C. with mild agitation. Beads were collected by centrifugation. After 3 washes with cold low or high stringency lysis buffer, pelleted beads were quenched in protein sample buffer and boiled. Supernatants were retrieved and analyzed by immunoblot using antibodies directed against α-SMA, β-actin, SMMHC, HDAC8, HDAC1 or HDAC3.

siRNA Transfection

All siRNAs used in this study were made of 2 complementary nucleotide strands containing 19 RNA bases followed by 2 DNA bases (T). They were chemically synthesized and PAGE purified (Eurogentec, Seraing, Belgium). The following oligonucleotides sequences were used: 5'-UGAGCCCACCGAAUCCAATT-3' (SEQ ID NO:8) and 5'-UUGGAUUCGGUGGGCUCATT-3' (SEQ ID NO:9) for HDAC8 siRNA#1; 5'-ACGGGCCAGUAUGGUGCAUTT-3' (SEQ ID NO:10) and 5'-AUGCACCAUACUGGCCCGUTT-3' (SEQ ID NO:11) for HDAC8 siRNA #2; and 5'-CUGCAAGGGAUGGAUCUGATT-3' (SEQ ID NO:16) and 5'-UCAGAUCCAUCCCUUGCAGTT-3' (SEQ ID NO:17) for HDAC6 siRNA. This HDAC6 siRNA has been previously shown to efficiently silence HDAC6 expression. Each pair of oligonucleotides was annealed at a concentration of 20 µM in 50 mM Tris pH 7.5-8.0, 100 mM NaCl. Calcium phosphate-mediated transfection was performed in 10-cm Petri dishes with a final concentration of 20 nM of each siRNA, unless otherwise specified. HDAC6 siRNA was added to the transfection medium at a final concentration of 40 nM.

Cells were plated approximately 24 hours before transfection and the medium was changed 1 hour prior to transfection.

Cells were transfected at a starting confluence between 40% and 60%. After transfection, cells were incubated in 10% FBS medium and collected 48 hours later. In some experiments, cells were transfected 3 times over 4 days and collected 24 hours after final transfection. For collagen contraction assays, cells were transfected twice over 2 days and added to the hydrated collagen lattices 48 hours after the second transfection. Mock transfections with transfecting reagent alone served as negative control.

Contraction of Hydrated Collagen Lattices

Collagen I was acid-extracted from newborn bovine skin, as previously described. Delvoye et al. (1983) supra; Bell et al. (1979) *Proc. Natl. Acad. Sci. USA* 76:1274-1278. Collagen was dissolved at 1 mg/mL in sterile 0.1% acetic acid. Collagen gel contraction assays were essentially performed as described. Delvoye et al. (1991) *J. Invest. Dermatol.* 97:898-902. Briefly, concentrated DMEM, bicarbonate buffer solutions and collagen were mixed on ice to yield a neutralized collagen gel solution. HSMCs were added to this collagen solution to obtain a cellular suspension containing $8 \times 10^3$ cells/mL in 0.3 mg/mL collagen, 1×DMEM, 10% FCS, 25 mM sodium bicarbonate, 2 mM glutamine, 50 µg/mL ascorbic acid, 100 units/mL penicillin and 100 µg/mL streptomycin. Samples (5 ml) of the cell/collagen mixtures were pre-warmed for approximately 5 minutes at room temperature, placed in 60-mm plastic bacteriological dishes, and then incubated at 37° C. in a humidified $CO_2$ incubator to allow gel polymerization.

Relaxation of the polymerized lattices was initiated one hour later by dislodging them from the surrounding plastic surface with a gentle rocking movement. Gels were allowed to contract for several days at 37° C. in the cell culture incubator. The contracted gels were photographed and the area of the gels was measured at defined time intervals. A minimum of 3 lattices was assayed per experimental condition. The contraction percentage was calculated by reporting the area of retracted lattice to the surface of the dish. Mean values are expressed±standard deviation of the mean. Experiments were performed at least 3 times.

In parallel with the collagen contraction assays, in vitro grown HSMCs subjected to the same experimental conditions (transfections) as those included in the contraction assay were lysed in protein lysis buffer at the time cells assayed for gel contraction were added to the collagen matrices. Protein lysates were analyzed by immunoblot as described above. Similar dilutions of HSMC suspensions were also reseeded in plastic culture dishes at the time HSMCs assayed for gel contraction were added in the collagen matrices in order to assess cell morphology. Morphology of the cells was also routinely examined before trypsinization and subsequent reseeding. Photomicrographs of the cell monolayers were taken with a Leica microscope at different times before and after the start of the gel contraction.

Results

HDAC8 Associates with α-SMA in Vitro and in Vivo

Figure 4A:
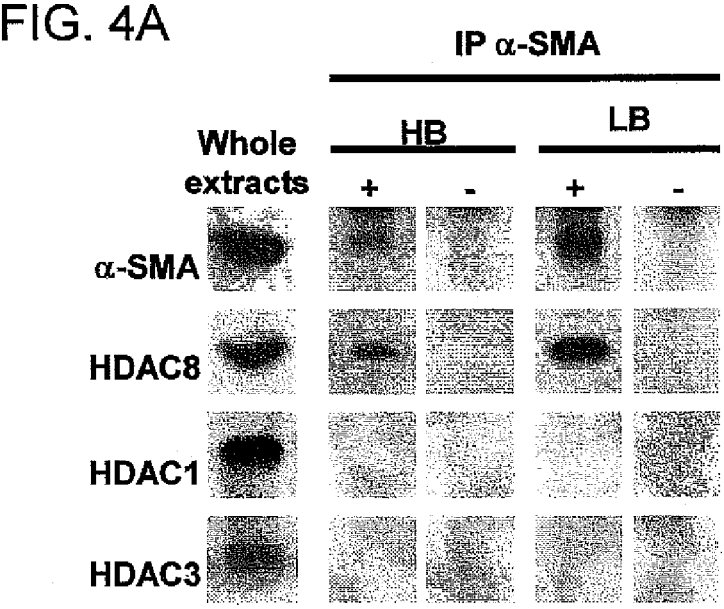
FIGS. 4A and 4B depict co-immunoprecipitation of HDAC8 and α-SMA in primary human smooth muscle cells (HSMCs).
Figure 4B:
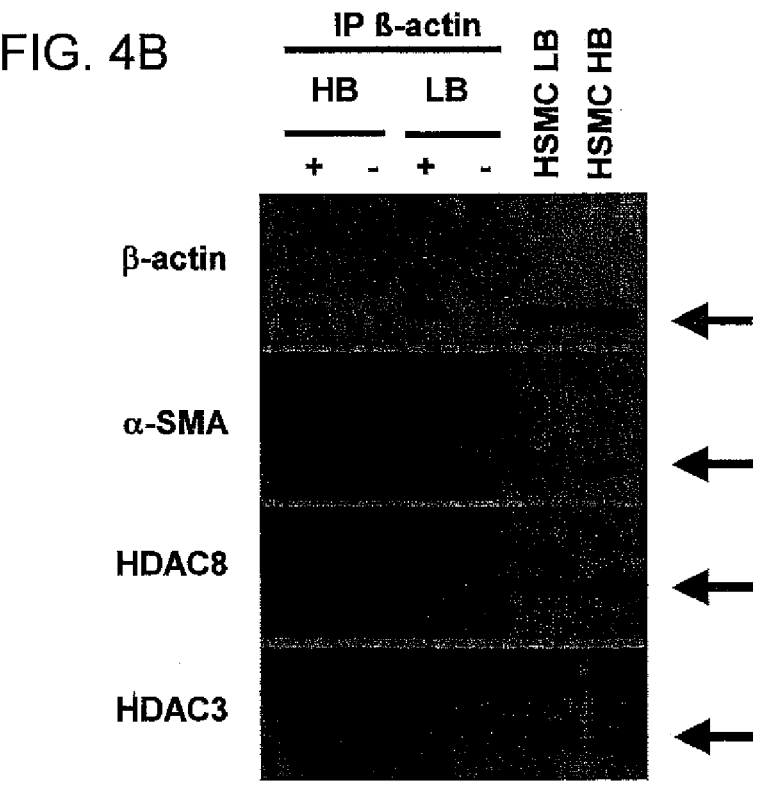

As shown in Example 1, HDAC8 is a novel marker of smooth muscle differentiation with a predominant cytosolic localization, and displays a striking cytoskeleton-like pattern of distribution reminiscent of actin stress fibers in cultured HSMCs. Notably, epitope-tagged HDAC8—but not HDAC3 or HDAC6—overexpressed in murine NIH-3T3 fibroblasts forms cytoplasmic stress fibers-like structures that co-localize with α-SMA, suggesting a possible specific association of HDAC8 with this smooth muscle cytoskeletal protein. To investigate whether HDAC8 may associate with α-SMA, performed coimmunoprecipitation experiments were performed in which endogenous α-SMA was pulled down from HSMC total protein lysates with the use of a monoclonal anti-α-SMA antibody that specifically recognizes the NH2-terminal sequence Ac-EEED of the protein. Chaponnier et al. (1995) *J. Cell Biol.* 130:887-895. The immunoprecipitates were subjected to immunoblot using antibodies directed against HDAC8, HDAC1 and HDAC3. As shown in FIG. 4A, HDAC8 coimmnunoprecipitated with α-SMA while HDAC1 and HDAC3, two other class I HDACs, were not detected in the immunocomplexes. When the anti-α-SMA antibody was replaced with mouse IgG of the same isotype, as negative control for immunoprecipitation, no α-SMA, HDAC8, HDAC1 or HDAC3 was found in the immunoprecipitates (FIG. 4A). Similar results were obtained when cell lysates were prepared with 2 different lysis buffers of low or high stringency (FIG. 4A). To search for a possible association between HDAC8 and another actin isoform, similar pull down assays were carried out with the use of a monoclonal anti-β-actin antibody. As shown in FIG. 4B, no α-SMA, HDAC8 or HDAC3 protein was detected in the β-actin-containing immunocomplexes. Communoprecipitation experiments were also performed with the use of protein lysates from normal human prostate tissues, which are highly enriched in HDAC8-expressing myofibroblasts.

FIGS. 4A and 4B. Co-immunoprecipitation of HDAC8 and α-SMA. Protein lysates from primary human smooth muscle cells (HSMCs) were immunoprecipitated with antibodies against α-SMA (FIG. 4A) or β-actin (FIG. 4B), as described in Materials and Methods. Immunoprecipition with IgG2a was used as a negative control Supernatants were analyzed by immunoblot using antibodies directed against α-SMA, β-actin, HDAC8 (N-20), HDAC1 and HDAC3. Total protein lysates from HSMCs were loaded on the gel as controls.

Figure 5:
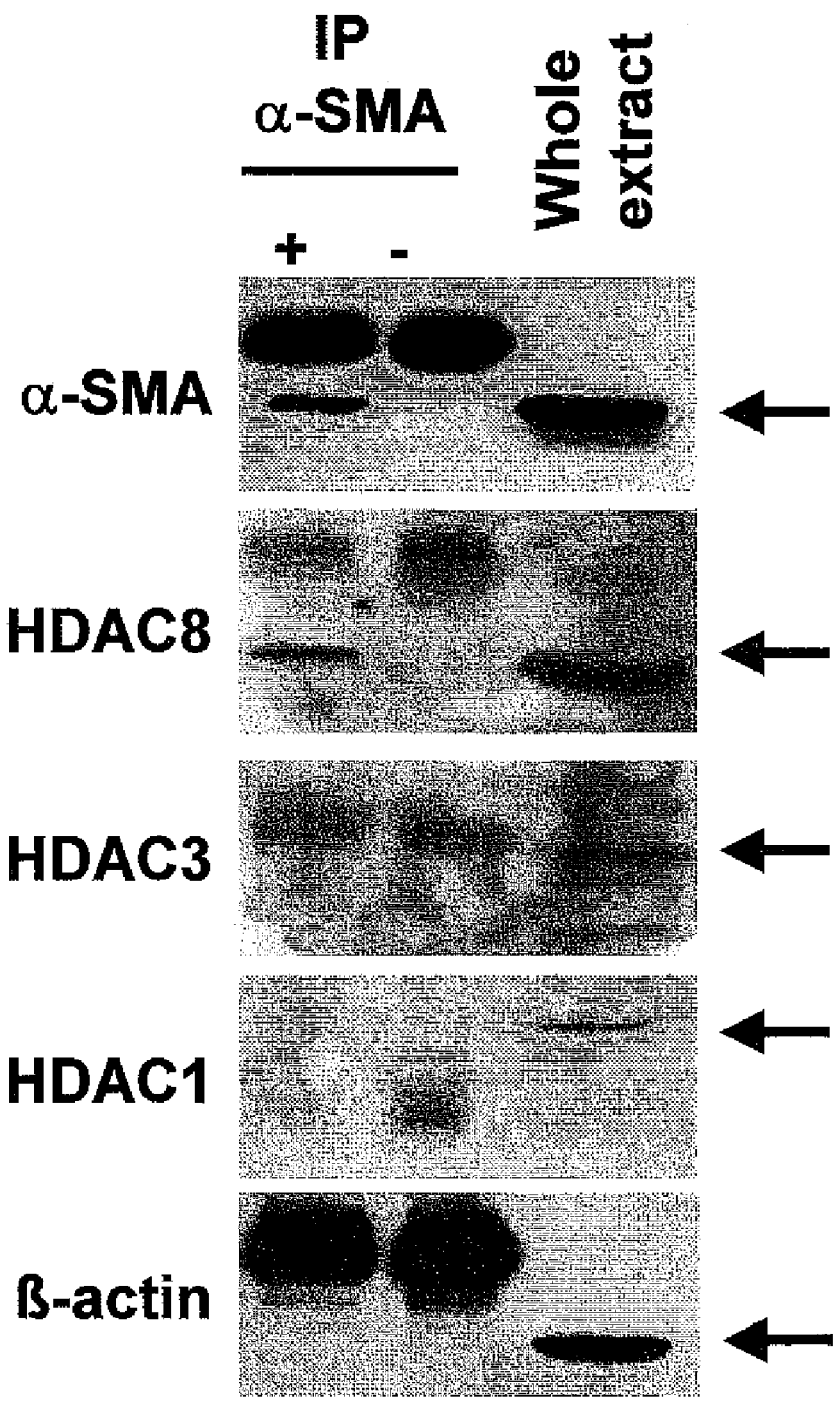
FIG. 5 depicts co-immunoprecipitation of HDAC8 and α-SMA in human prostate tissues.

FIG. 5. Co-immuno co-immunoprecipitation of HDAC8 and α-SMA in normal prostate tissues. Protein lysates from human prostate tissues were immunoprecipitated with antibodies against α-SMA, as described in Materials and Methods. Immunoprecipitation with IgG2a was used as negative control. Supernatants were analyzed by immunoblot using antibodies directed against α-SMA, HDAC8 (N-20), HDAC1, HDAC3, and β-actin. A whole protein extract from prostate tissues was loaded on the gel as control.

HDAC8 RNA Interference Impairs the Capacity of HSMCs to Contract Collagen Lattices The observation that HDAC8 may specifically associate with a smooth muscle cytoskeleton protein lead to the hypothesis that HDAC8 may be involved in the regulation of the smooth muscle contractile apparatus. To test this hypothesis, used RNA interference was used to determine the effect of a reduction of HDAC8 abundance in HSMCs upon the capability of these cells to contract collagen I lattices in vitro.

Figure 6A:
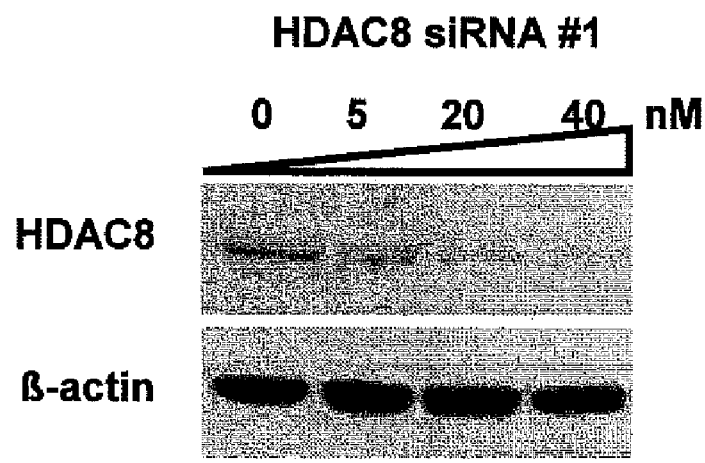
FIGS. 6A and 6B depict a dose curve of HDAC8 siRNA#1 (FIG. 6A); and the specific reduction of HDAC8 expression in cell lines after transfection with HDAC8 siRNA#1 (FIG. 6B).

Primary HSMCs were transfected with two different siRNAs specific for HDAC8:HDAC8 siRNA#1, which targets a 3' region of HDAC8 mRNA upstream of the stop codon, and HDAC8 siRNA#2, which recognizes a 5' region located close to the start codon of the transcript. To determine the optimal concentration of siRNAs, HSMCs were transfected with HDAC8 siRNAs at concentrations of 0, 5, 20 or 40 nM. As shown in FIG. 6A, immunoblot analysis of HDAC8 expression in these cells indicated that the reduction of HDAC8 abundance in HSMCs by HDAC8 siRNA#1 was siRNA concentration-dependent, with a marked reduction at 20 nM or 40 nM. The amount of β-actin protein was not affected by transfections with various concentrations of HDAC8 siRNA#1 (FIG. 6A). On the basis of these results, all further transfections with HDAC8 siRNAs in this study were performed with a final concentration of 20 nM.

Figure 6B:
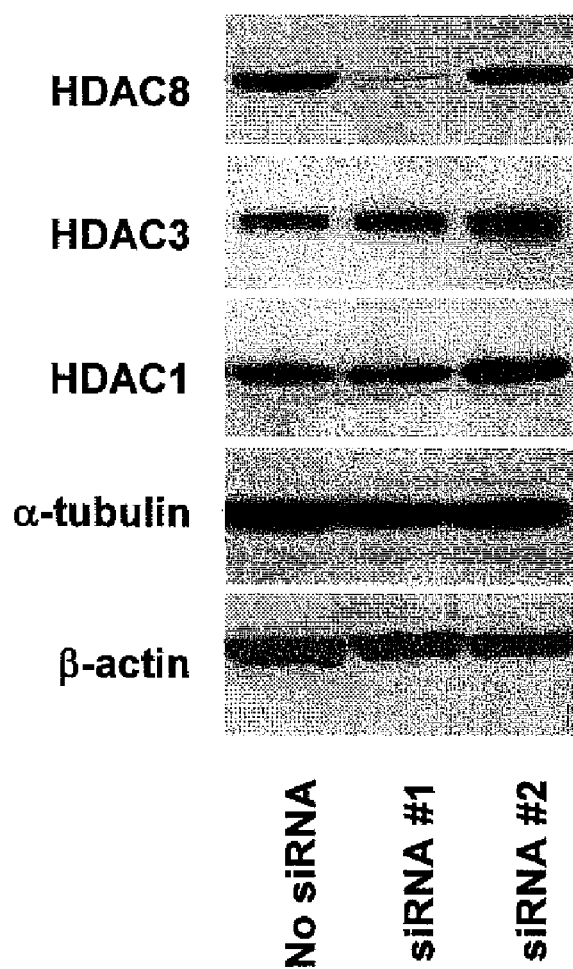

HDAC8 siRNA#1 transfection was able to induce a substantial silencing of HDAC8 expression in HSMCs (FIGS. 6A and 7B) as well as in NIH-3T3 cells, which also express HDAC8 (FIG. 6B). However, transfections with HDAC8 siRNA#2 were inefficient to reduce HDAC8 abundance in these cell lines (FIGS. 6B and 7B). Thus, among 2 HDAC8 siRNAs tested, only one of them had a suppressive effect on HDAC8 protein expression. HDAC8 siRNA#2 was used as an additional negative control together with mock transfections carried out without siRNAs in the transfection medium.

In order to verify that HDAC8 siRNAs induced the specific degradation of HDAC8 transcripts, NIH-3T3 cells and HSMCs were transfected with HDAC8 siRNA#1 or HDAC8 siRNA#2 and the expression levels of other class I HDACs (HDAC1 and HDAC3), which share a high sequence homology with HDAC8, were assessed. We have observed that, even following 3 transfections over 4 days, the expression levels of HDAC1 and HDAC3 as well as those of cytoskeletal β-actin and α-tubulin proteins were not reduced by HDAC8 siRNA#1 or siRNA#2 transfections in NIH-3T3 cells (FIG. 6B) or HSMCs.

FIGS. 6A and 6B. 6A) Dose-curve of HDAC8 siRNA#1 Smooth muscle cells from human umbilical cord vein (HSMCs) were transfected for 16 hours with HDAC8 siRNA#1 at a final concentration of 0 nM, 5 nM, 20 nM, or 40 nM, using the calcium phosphate precipitation method, as described in Materials and Methods. Cells were lysed in protein extraction buffer 48 hours after transfection, and lysates were subjected to immunoblot analysis of HDAC8 and β-actin expression, as described in Materials and Methods. 6B) Reduction of HDAC8 expression in NIH-3T3 fibroblasts after transfection with HDAC8 siRNA#1. Murine NIH-3T3 fibroblasts were transfected 3 times over 4 days without siRNA (mock), with HDAC8 siRNA#1 or with HDAC8 siRNA#2, using the calcium phosphate precipitation method, as described in Materials and Methods. Cells were lysed in protein extraction buffer 24 hours after the last transfection and lysates were subjected to immunoblot analysis of HDAC1, HDAC3, HDAC8 expression, α-tubulin and β-actin, as described in Materials and Methods.

FIGS. 7A and 7B. 7A) Schematic representation of the experimental protocol used to assess the impact of HDAC8 expression silencing by RNA interference on the contraction capability of HSMCs in a collagen contraction assay. HSMCs were transfected twice over 2 days without siRNA, with HDAC8 siRNA#1, with HDAC8 siRNA#2, or with HDAC6 siRNA, using the calcium phosphate precipitation method, as described in Materials and Methods. Forty-eight hours after the second transfection, cells were either (i) incubated in collagen solution and assayed for collagen gel contraction, (ii) lysed in protein extraction buffer and lysates were subjected to immunoblot analysis, or (iii) reseeded onto plastic dishes to assess cellular morphology, as described in Materials and Methods. 7B) Reduction of target gene expression with various siRNAs at the start of the collagen contraction assay HSMCs were transfected with or without siRNAs as indicated in Materials and Methods. Protein lysates were subjected to immunoblot analysis of HDAC8, acetylated-α-tubulin, and β-actin expression as described in Materials and Methods.

In order to determine whether HDAC8 may participate in the mechanisms conferring contractile capacity to smooth muscle cells, HSMCs were transfected twice over 48 hours without siRNA, with HDAC8 siRNA#1, with HDAC8 siRNA#2 or with HDAC6 siRNA. Forty-eight hours after the second transfection, HSMCs were either lysed in protein extraction buffer for immunoblot analysis, assayed for collagen gel contraction, or reseeded on plastic dishes to evaluate their morphology (FIG. 7A).

Immunoblot blot analysis was employed to examine the HDAC8 content and α-tubulin acetylation level of the cells. Protein lysates subjected to immunoblot analysis were extracted exactly at the time when transfected cells were incubated in the collagen solution in order to ensure that these cells displayed reduced target gene expression with the various siRNAs at the start of the collagen contraction assay. FIG. 7B shows that the amount of HDAC8 protein was decreased only in cells transfected with HDAC8 siRNA#1. HDAC6 is an α-tubulin deacetylase (Haggarty et al. (2003) *Proc. Natl. Acad. Sci. USA* 100:4389-4394; Hubbert et al. (2002) *Nature* 417:455-458; Matsuyama et al. (2002) *EMBO J.* 21:6820-6831; and North et al. (2003) *Mol Cell* 11:437-333). The efficiency of HDAC6 silencing by HDAC6 siRNA was indirectly determined by analysing the amount of acetylated α-tubulin. It was observed that only HSMCs transfected with siRNAs specific for HDAC6 displayed increased levels of acetylated α-tubulin. The levels of β-actin were unaffected by the various transfections. These results indicated that the targeted HDACs were at least partially silenced when HSMCs were incubated in the collagen lattices. The ability of HDAC8-silenced, HDAC6-silenced, and control cells to contract a collagen lattice into which they had been incubated was compared.

FIG. 8. The impact of HDAC8 siRNA#1 silencing on the ability of HSMCs to contract collagen lattices. Gel contraction was allowed to proceed for 144 h. A minimum of 3 lattices was assayed per experimental condition. The area of the gels was measured at defined time intervals. The area of contracted lattices was calculated as a percentage of the surface of the dish. Mean values are expressed ±standard deviation of the mean. Experiments were performed at least 3 times and similar results were obtained. The results of a representative experiment are shown.

Collagen lattices were photographed 24 hours after release of the lattices. At that time point, the mean area of the lattices containing HDAC8 siRNA#1-transfected HSMCs was 8 to 9 times larger than the mean area of the lattices incubated with mock or HDAC8 siRNA#2-transfected HMSCs and 4.8 times larger than the mean area of lattices incubated with HDAC6-silenced HSMCs. This strong contraction inhibition obtained with HDAC8 siRNA#1-transfected HSMCs persisted over a 6 days period (FIG. 8). These experiments were performed at least three times and similar results were obtained.

HDAC8 RNA Interference Induces Morphological Changes in HSMCs

The morphology of siRNA-transfected HSMCs was assessed before and after reseeding at the time when transfected HSMCs were added into the collagen matrices. Before trypsinization and reseeding, no evident change in cellular morphology was noted by light microscopy examination. As compared with mock-transfected HSMCs, HDAC8 siRNA#2- and HDAC6 siRNA-transfected HSMCs exhibited no obvious modification in cell shape or size at any time after reseeding. Strikingly, HDAC8 siRNA#1-transfected HSMCs exhibited a noticeable reduction in size with decreased cell spreading. These morphological changes were noted as early as one hour after replating and were maintained for approximately one week. Thereafter, cellular morphology resumed to that of control HSMCs.

Example 3

Novel Smooth Muscle Markers Reveal Abnormalities of the Intestinal Musculature in Human Gastrointestinal Motility Disorders Materials and Methods
Tissue Samples Full thickness biopsies or resected intestinal segments were obtained from patients with chronic intestinal pseudoobstruction (CIPO), duodenal atresia, Hirschsprung's disease, idiopathic megacolon, and slow-transit constipation (see Table 2 for details). Age-matched control specimens of colon (n=12), ileum (n=5) and duodenum (n=3) were obtained from patients with diseases unrelated to GI motility disorders. The use of these human tissues was approved by the Medical Institutional Ethics Committees of the Faculté de Médecine, Université Libre de Bruxelles, Brussels, Belgium, and of the Faculty of Medicine, University of Lübeck, Germany.

TABLE 2

Description of diseased specimens and histopathology of the ENS/ICC

| Diagnosis | Tissue | Number of patients | Age | ENS/ICC histopathology |
|---|---|---|---|---|
| CIPO | colon, ileum | 2 | 1 year, 16 years | no abnormality |
| Duodenal atresia | duodenum | 1 | neonatal | no abnormality |
| Hirschsprung's disease | colon (ganglionic + aganglionic) | 4 | neonatal - 19 years | aganglionosis deficiency of ICC* |
| Idiopathic megacolon | colon | 2 | 3 years, 6 years | no abnormality |
| Slow-transit constipation | colon | 4 | 21-58 years | hypoganglionosis deficiency of ICC* |

Preparation of Samples for Immunohistochemistry

Immediately after surgery, specimens were fixed overnight in fresh 4% paraformaldehyde solution in phosphate-buffered saline (PBS), pH 7.4, at 4° C., cryopreserved in graded solutions of sucrose (10%, 20%, 30%; overnight each), embedded in Tissue-Tek OCT compound (Miles, Elkhart, Ind.), snap-frozen in 2-methylbutane that had been cooled on dry ice and stored at −80° C. Sections (15 µm thick) were cut on a cryostat, mounted onto slides coated with 0.1% poly-L-lysine and stored at −20° C. until use.

Immunohistochemistry

Immunohistochemistry was carried out at room temperature using the avidin biotin-complex (ABC) system (Vectastain ABC Elite), according to the instructions of the supplier (Vector, Burlingame, Calif.). Briefly, sections were incubated with 0.3% hydrogen peroxide in methanol for 30 min to block endogenous peroxidase activity, rinsed 3 times in 10 mM TRIS in 0.15 M sodium chloride, pH 7.4 (TRIS-buffered saline, TBS), containing 0.1% (v/v) Triton X-100 (TBS-TX), incubated for 20 min in 10% normal horse serum (NHS) (Hormonologie Laboratoire, Marloie, Belgium) in TBS-TX to reduce background staining, incubated with the primary antibody (Table 3) diluted in TBS containing 1% NHS for 24 h, rinsed in TBS for 10 min, incubated with biolinylated donkey anti-mouse or donkey anti-goat IgG (1:200, Jackson Immuno Research, PA) for 30 min, rinsed in TBS and incubated with ABC conjugated with horseradish peroxidase for 1 h. The peroxidase activity was revealed for 5 min with a solution containing 0.2 mg/mm 3,3'-diaminobenzidime (DAB) (Sigma) and 0.03% v/v $H_2O_2$ in 0.05 M TBS. For immunofluorescence stainings slides were incubated in the dark for 1 h at room temperature in TBS containing secondary antibodies coupled to FITC (1:200, Jackson Immuno Research, PA). Nuclear counterstaining was carried out with TOTO-3, a nucleic-acid-binding molecule fluorescent in the far-red spectrum (T-3604, Molecular Probes, Eugene, Oreg.), 5 µM in TRIS-HCl 0.05 M (pH 7.4), containing 0.5 mg/ml ribonuclease A (type 1-AS from bovine pancreas), for 2 h in the dark at room temperature. Optimal working dilutions had been previously determined empirically by serial dilutions for each antibody used. Omission of one of the primary or one of the secondary antibodies resulted in the absence of the corresponding labeling.

Prior to the immunohistochemical study with antibodies listed in Table 3, all specimens had been subjected to a histopathologic examination of the enteric nerve plexus, ICC and intramural lymphocyte distribution, using primary antibodies directed against Protein Gene Product (PGP) 9.5 (1:2000, rabbit polyclonal, Ultraclone, Isle of Wight), human Kit (1:1000, goat polyclonal, SC39, Santa Cruz Biotechnology, CA) and CD3 (1:50, mouse monoclonal, BD Biosciences, San Jose, Calif.) to visualize enteric nerves, ICC and T-lymphocytes, respectively, according to the protocol described above.

TABLE 3

Antibodies used for labeling smooth muscle cells

| Antibody | Specie | Source | Dilution | Binding site |
|---|---|---|---|---|
| Anti-smooth muscle α-actin, Cy3 conjugated (α-SMA) | mouse monoclonal | Sigma C-6198 | 1:1000 | N-terminal synthetic decapeptide of smooth muscle α-actin |
| Anti-smooth muscle myosin heavy chain (SMMHC) | mouse monoclonal | Sigma M-7786 | 1:1000 | myosin heavy chain polypeptides of 204 and 200 kDa |
| Anti-smoothelin (R4A) (SM) | mouse monoclonal | (van der Loop et al., 1996) | 1:100 | polypeptide of app 69 kDa (cytoskeleton-associated protein) |
| Anti-histone deacetylase 8 (HDAC8) | goat polyclonal | Santa Cruz Biotechnology (sc-11544, N20) | 1:1000 | peptide mapping at the amino terminus of human HDAC8 |

Routine Histology

Hematoxylin/eosin staining was used to evaluate the quality of the sections before immunostaining and the general histologic appearance, in particular to rule out inflammatory infiltrations or vacuolar degeneration of the intestinal musculature. In addition, Masson's trichrome staining was used to assess the distribution and amount of connective tissue components and to rule out fibrotic alterations of the smooth muscle layers.

Results

Control Specimens

Smooth Muscle Markers

While most specimens showed a homogeneous pattern of immunostaining for the smooth muscle markers used, a subgroup of samples from all diseases studied showed defective immunostaining patterns, mainly in the circular smooth muscle layer (Table 4). Either a complete lack of immunoreactivity or a patchy pattern with scattered "islets" of remaining immunoreactive smooth muscle cells were observed. When the circular smooth muscle layer was diffusely affected, its inner border appeared usually rather spared.

TABLE 4

Summary of routine histology and immunohistochemistry

| Diagnosis | Tissue | HE/TC | α-SMA-ir | Smoothelin-ir | HDAC8-ir | SMMHC-ir |
|---|---|---|---|---|---|---|
| CIPO | ileum | normal | lack | lack | lack | lack* |
|  |  |  | CM | CM | CM | CM |
|  | colon | normal | normal | lack* | lack* | lack* |
|  |  |  |  | CM | CM | CM |
| Duodenal atresia | duodenum | normal | normal | normal | lack* | lack* |
|  |  |  |  |  | CM | CM |
| Hirschsprung's disease | colon (ganglionic) | normal | normal | normal | lack | lack |
|  |  |  |  |  | CM + LM | CM + LM |
|  | colon (aganglionic) | normal | normal | lack | lack* | lack* |
|  |  |  |  | CM + LM | CM + LM | CM |
| Idiopathic megacolon | colon | normal | normal | lack* | lack* | lack* |
|  |  |  |  | CM + LM | CM + LM | CM + LM |
| Slow-transit constipation | colon | normal | normal | lack | lack | lack |
|  |  |  |  | CM | CM | CM |

*focal lack; TC, Masson's trichrome; HE, hematoxylin/eosin; CM, circular muscle layer; LM, longitudinal muscle layer; ir, immunoreactivity General Histology, ENS, and ICC Hematoxylin/eosin and Masson's trichrome staining confirmed the normal histomorphology of the specimens. In particular, the smooth muscle layers displayed a normal appearance without signs of degeneration or lymphocytic infiltration. The enteric nerve plexus and the networks of ICC were normally distributed.

Smooth Muscle Markers

α-SMA, SMMHC, SM and HDAC8 immunoreactivity decorated all smooth muscle structures within the intestinal wall, namely the longitudinal and circular layers of the muscularis propria, the lamina muscularis mucosae, the subepithelial myofibroblasts and the tunica media of blood vessels. On these tissue sections, the cytoplasm of smooth muscle cells consistently appeared uniformly stained sparing out the nuclei.

Diseased Specimens

General Histology, ENS, and ICC

The smooth muscle layers showed neither fibrotic, inflammatory nor degenerative processes on hematoxylin/eosin and Masson's trichrome staining. All specimens displayed a normal distribution of CD3-immunoreactive lymphocytes located intraepithelially, within the outer portion of lymph follicles and sparsely scattered throughout the lamina propria. No signs of lymphocytic infiltration, in particular of smooth muscle layers or enteric ganglia, were observed.

As previously reported, patients with Hirschsprung's disease showed an aganglionosis within the distal part of the colon, while patients with slow-transit constipation revealed a relative loss of myenteric nerve cells (oligoneuronal hypoganglionosis). Both groups were additionally characterized by a relative loss of ICC (Table 2). These data have been presented in detail in a previous study (Wedel et al. (2002) *Gastroenterology* 123:1459-1467).

Adjacent blood vessels and the muscularis mucosae were consistently normally labeled, ruling out improper tissue handling or poor fixation. Furthermore, sections from the same specimens had previously shown uniform results for Kit-, PGP 9.5- and CD3 immunohistochemistry.

The various smooth muscle markers used detected these alterations with variable frequency. While α-SMA-immunoreactivity was generally unsuspicious (except for one specimen), immunoreactivity for SM, SMMHC and HDAC8 was altered in most of the diseased cases (Table 4). Noteworthy, alterations of the distribution of SM, SMC and HDAC8 immunostaining was not always concordant e.g.: a specimen of Hirschsprung's disease stained normally for α-SMA, but showed a complete lack of SM immunoreactivity, a focal absence of HDAC8 immunoreactivity in both muscle layers, and a focal lack of SMMHC immunoreactivity confined to the circular muscle layer.

Moreover, different patterns of abnormal immunoreactivity were also observed in different gut segments specimens obtained from the same patient, e.g. ileum versus colon in a case of CIPO or ganglionic versus aganglionic colon in a case of Hirschsprung's disease.

Example 4

Screening of Histone Deacetylases (HDAC) Expression in Human Prostate Cancer Reveals Distinct Class I HDAC Profiles Between Epithelial and Stromal Cell Materials and Methods Cell Lines, Tissue Culture, and Reagents PC-3, DU-145 and LNCaP human prostate cancer cell lines were purchased from the American Type Culture Collection (Rockville, Md., USA). Cells were routinely grown in RPMI-1640 supplemented with 10% decomplemented fetal bovine serum and 2 mM L-glutamine at 37° C. in a humidified 95% air/5% $CO_2$ atmosphere. All tissue culture reagents were obtained from Invitrogen (Merelbeke, Belgium) unless otherwise specified.

Patients and Tissues

Fresh as well as formalin-fixed paraffin-embedded normal and cancerous prostate tissue samples were obtained from patients who had undergone a radical prostatectomy for clinically localized prostate cancer in the Department of Urology at the University Hospital of Liège, Belgium, during the period from 1996 through 2001. None of the patients included in this study had received preoperative hormonal or radiation therapy. All patients had a clinically confined tumor, classified as stage T1 or T2 N0M0, according to the TNM system. Schroeder et al. (1992) *The Prostate (Suppl)* 4:129-138. Absence of regional or distant extension of the tumor was assessed before surgery by chest x-ray, pelvic computed tomography scan, and bone scanning. All patients had undergone a bilateral ilio-obturator lymphadenectomy prior to excision of the prostate gland and histopathological examination of the resected lymph nodes had shown absence of tumor infiltration. The Ethics Committee of the University Hospital of Liège approved the specific protocol used in this study.

Fresh Human Prostate Tissue Harvesting and Processing

In order to evaluate HDAC1, HDAC2, HDAC3, HDAC4, HDAC5, HDAC6, HDAC7 and HDAC8 protein and mRNA expression in non-neoplastic and neoplastic prostate tissues from the same patient by use of Western blotting and quantitative RT-PCR, respectively, fresh samples of normal and malignant prostate tissue were harvested from radical prostatectomy specimens according to a previously described method. Wheeler et al. (1994) *Prostate* 25:274-279; and van den Brule et al. (2001) *J Pathol.* 193:80-87. Briefly, tissue samples were taken from the peripheral and transitional zones using a 6- or 8-mm diameter punch biopsy instrument (Stiefel laboratories, Leuven, Belgium). Two one millimeter-thick slices were immediately sectioned from both ends of each fresh cylinder-shaped sample and either included in Tissue-Tek® OCT (Optimum Cut Medium) compound (Miles Inc., West Haven, Conn.), frozen in liquid nitrogen vapors and stored at −80° C., or fixed in 10% phosphate buffered formalin overnight, dehydrated in graded alcohols, and paraffin embedded. The remaining cylinder was flash-frozen in liquid nitrogen and then stored at −80° C. for subsequent RNA and protein isolation. Five μm thick sections were cut from the tissue slices and stained with hematoxylin and eosin (H&E). Stained sections were examined under the microscope to determine the presence and extent of areas of normal glandular prostate tissue, prostate intra-epithelial neoplasia (PIN), and adenocarcinoma. Snap-frozen tissue cylinders containing prostate cancer were selected for immunoblot and RT-PCR experiments only when cancer cells areas represented at least 50% of the total surface of the corresponding H&E stained sections.

Antibodies

Expression of HDAC1 was examined by immunohistochemistry and immunoblot techniques with the use of 3 different anti-HDAC1 sera: (i) a specific anti-HDAC1 serum raised against a peptide corresponding to the predicted C-terminal domain of human HDAC1 (amino acids 467-482) (Emiliani et al. (1998) *Proc. Natl. Acad. Sci. USA* 95:2795-2800), (ii) a rabbit polyclonal anti-HDAC1 antibody raised against a peptide corresponding to amino acids 53-482 of mouse HDAC1 (Upstate Biotechnology, Lake Placid, N.Y., USA), and (iii) a polyclonal anti-HDAC1 antibody raised against a synthetic peptide corresponding to the C-terminus of human HDAC1 (Cell Signaling Technology Beverly, Mass., USA). These antibodies are herein referred as Ab1, Ab2, and Ab3, respectively. Expression of HDAC5 and HDAC8 proteins was investigated by immunoblot and immunohistochemistry using commercially available polyclonal anti-HDAC5 (Cell Signaling Technology Beverly, Mass., USA) and anti-HDAC8 (N-20) (Santa Cruz Biotech., Inc., Santa Cruz, Calif.) antibodies, respectively. The anti-HDAC8 antibody was raised against a peptide mapping at the amino terminus of HDAC8 of human origin (Santa Cruz Biotech., Inc., Santa Cruz, Calif.).

RNA and Protein Extraction

HDAC1-8 protein and transcript expression was examined in normal and malignant human prostate tissue specimens as well as in LNCaP, DU-145 and PC-3 cells. Pulverization of the snap-frozen prostate tissues was performed with the use of a Mikro-Dismembrator U (Braun Biotech., Melsungen, Germany) and generated tissue powder that was immediately processed for protein and RNA extraction. Total RNA was extracted from 20-50 mg of each tissue homogenate with the use of the RNeasy mini kit (Qiagen, Inc., Valencia, Calif.), according to the manufacturer's protocol. The remaining tissue powder was lysed in 1% sodium dodecylsulfate (SDS) for protein extraction. After rinses in PBS (PBS w/o calcium, magnesium, and sodium bicarbonate), in vitro grown human prostate cancer cells (at a confluence of ±60%) were scrapped in presence of either 1% SDS for protein extraction or RNeasy lysis buffer for RNA isolation.

Immunoblot

Equal amounts of protein extracts (as determined by a bicinchoninic acid determination kit [Pierce Chemical Co., Rockford, Ill., USA]) were separated by electrophoresis in 10% SDS-polyacrylamide gels and transferred to polyvinylidene difluoride membranes (Immunobilon, Millipore Corp., Bedford, Mass., USA), which were stained with Ponceau S (Sigma Chemical Company, St. Louis, Mo.) to examine the equal protein sample loading and transferring. The membranes were blocked with 5% non-fat dry milk in Tris-buffered saline (20 mM Tris base [pH 7.6], 150 mM NaCl) containing 0.1% Tween-20 (TBS-T), and probed with an anti-HDAC1 (Ab1, Ab2, or Ab3, see 'Antibodies'), anti-HDAC5 or anti-HDAC8 antibody. After washing in TBS-T, membranes were incubated with horseradish peroxidase (HRP)-conjugated secondary antibodies (Bio-Rad Laboratories, Hercules, Calif.) and developed using an enhanced chemiluminescence detection system (ECL detection kit; Amersham Corp., Arlington Heights, Ill.), according to the instructions of the manufacturer. Membranes were exposed to Kodak X-Omat AR films, stripped at 60° C. for 1 hour in Tris buffer (80 mM, pH 6.7) containing 2% SDS and 0.25 M 2-mercaptoethanol, washed in TBS-T and then reprobed with an anti-cytokeratin 18 (CK18) monoclonal antibody (CY-90, Sigma, Mich., USA). The immunoblots were quantitated by densitometric analysis using the NIH Image 1.6.2. software (NIH, Bethesda, Md.; http://rsb.info.nih.gov/nih-image/).

Real-Time Reverse Transcription-Polymerase Chain Reaction (RT-PCR).

Reverse Transcription

For cDNA synthesis, 1 μg of total RNA was reverse-transcribed in a 20 μl reaction mixture containing 250 μM of each dNTP, 20 U of RNase inhibitor, 50 U of MuLV Reverse Transcriptase (RT), 2.5 μM Random Hexamers, and 1× buffer (1.5M $MgCl_2$) (all reagents purchased from PE Applied Biosystems, Foster City, Calif.). The reaction mix was incubated at 42° C. for 45 min and then denatured at 99° C. for 5 min. Reactions not containing the RT or omitting the target RNA were used as controls.

Primers and Probes

Specific primers and probes for the human HDAC1, HDAC2, HDAC3, HDAC4, HDAC5, HDAC6, HDAC7 and HDAC8 genes (Table 5) were designed from sequences available in the GenBank database, using the Primer Express 1.0 Software (PE Applied Biosystems, Foster City, Calif.). The housekeeping CYCLOPHILIN and 18S rRNA, genes (control reagents kit, PE Applied Biosystems, Foster City, Calif.) were used as endogenous controls to normalize the amount of HDAC transcripts in each reaction. All sets of primers and probes were selected to work under identical cycling conditions. cDNA amplification products using HDAC primers had been previously checked to yield a single band of the expected size after electrophoretic migration in a 2% agarose gel stained with ethidium bromide. HDAC1, HDAC2, HDAC3, HDAC4, HDAC5, HDAC6, HDAC7 and HDAC8 probes were synthesized by PE Applied Biosystems.

Table 5 Sequences of HDAC Primers and Probes Used for Real-Time RT-PCR Experiments (SEQ ID NOs:18-41)

TABLE 1

Sequences of HDAC primers and probes used for Taqman® PCR experiments.

| Oligonucleotide name | Sequence |
|---|---|
| HDAC1 amplicon size: 102 bp | |
| HDAC1 forward primer | ACCGGGCAACGTTACGAAT |
| HDAC1 reverse primer | CTATCAAAGGACACGCCAAGTG |
| HDAC1 hybridization probe | CACCGCCTCCCAGCATCAGCA |
| HDAC2 amplicon size: 151 bp | |
| HDAC2 forward primer | TCATTGGAAAATTGACAGCATAGT |
| HDAC2 reverse primer | CATGGTGATGGTGTTGAAGAAG |
| HDAC2 hybridization probe | CCTTTTCCAGCACCAATATCCCTCAAGT |
| HDAC3 amplicon size: 87 bp | |
| HDAC3 forward primer | TTGAGTTCTGCTCGCGTTACA |
| HDAC3 reverse primer | CCCAGTTAATGGCAATATCACAGAT |
| HDAC3 hybridization probe | CTCTGCAAGGAGCAACCCAGCTGAA |
| HDAC4 amplicon size: 115 bp | |
| HDAC4 forward primer | AATCTGAACCACTGCATTTCCA |
| HDAC4 reverse primer | GGTGGTTATAGGAGGTCGACACT |
| HDAC4 hybridization probe | AACGCAGCACAGTTCCCTTGACCAG |
| HDAC5 amplicon size: 83 bp | |
| HDAC5 forward primer | TTGGAGACGTGGAGTACCTTACAG |
| HDAC5 reverse primer | GACTAGGACCACATCAGGTGAGAAC |
| HDAC5 hybridization probe | TGGTGATGCCCATTGCCCACG |
| HDAC6 amplicon size: 127 bp | |
| HDAC6 forward primer | TGGCTATTGCATGTTCAACCA |
| HDAC6 reverse primer | GTCGAAGGTGAACTGTGTTCCT |
| HDAC6 hybridization probe | CCCGCTATGCTCAACAGAAACACCG |

TABLE 1-continued

Sequences of HDAC primers and probes used for Taqman® PCR experiments.

| Oligonucleotide name | Sequence |
|---|---|
| HDAC7 amplicon size: 91 bp | |
| HDAC7 forward primer | CTGCATTGGAGGAATGAAGCT |
| HDAC7 reverse primer | CTGGCACAGCGGATGTTTG |
| HDAC7 hybridization probe | TGTCAGTGTCCACCCCAACCCCA |
| HDAC8 amplicon size: 78 bp | |
| HDAC8 forward primer | TCCCGAGTATGTCAGTATATGA |
| HDAC8 reverse primer | GCTTCAATCAAAGAATGCACCAT |
| HDAC8 hybridization probe | CCTGGCCAAGATCCCCAAACGG |

Real-Time PCR.

Taqman® PCR was performed on the cDNA samples using an ABI PRISM 7700 Sequence Detector (PE Applied Biosystems, Foster City, Calif.). The Taqman® PCR Core Reagent kit (PE Applied Biosystems) was used according to the manufacturer's directions with the following modifications: dUTP was replaced by dTTP at the same concentration, and incubation with AmpErase was omitted. For each sample tested, PCR reaction was carried out in a 50 µl volume containing 2 µl of cDNA reaction (equivalent to 100 ng of template RNA) and 2.5 U of AmpliTaq Gold® (PE Applied Biosystems). Oligonucleotide primers and fluorogenic probes were added to a final concentration of 100 nM each. After activation of AmpliTaq Gold® for 10 min at 94° C., amplification step consisted of 45 cycles of 94° C. for 45 sec, 58° C. for 45 see, and 72° C. for 30 sec.

In each experiment, 6 additional reactions with serial dilutions (50× magnitude) of a prostate cancer cell line cDNA as template were performed with each set of HDAC, cyclophilin, or 18S rRNA primers and probes in the same 96-well plate to generate standard curves relating the threshold cycle ($C_T$) to the log input amount of template. All samples were run in triplicates. PCR reactions with samples in which the reverse transcriptase or the target RNA was omitted from the RT reaction did not yield any significant amplification. The relative amounts of HDAC transcripts in each sample were determined using the standard curve method and were normalized to cyclophilin mRNA expression levels, as described in detail in ABI PRISM Sequence Detection System User Bulletin #2 (PE Applied Biosystems) and elsewhere. Fink et al. (1998) *Nat. Med.* 4:1329-1333. Relative HDAC transcript level in each cell line analyzed was calculated as a ratio between the HDAC mRNA level in the cell line investigated and the HDAC mRNA level in LNCaP cells. Relative HDAC mRNA level in each tumor/normal sample pair was calculated as a ratio between the HDAC mRNA level in the tumor sample and the HDAC mRNA level in the corresponding normal sample. The amplification efficiencies for HDAC1, HDAC5 and HDAC8 transcripts were also calculated. Because HDAC1 and HDAC5 amplification efficiencies were similar (HDAC1/HDAC5 relative efficiency trendline had a slope value of 0.01), HDAC1 and HDAC5 transcript levels could be compared with reasonable accuracy. Signoretti et al. (2000) *Am. J. Pathol.* 157:1769-1775.

In Situ Detection of HDAC1 and HDAC8 by Immunofluorescence and Immunoperoxidase in Human Non Malignant and Malignant Prostate Tissues and Cell Lines Immunfluorescence staining was performed using the ABC Vectastain Elite immunoperoxidase kit (Vector Laboratories, Inc., Burlingame, Calif., USA) and fluorescein isothiocyanate (FITC)-conjugated tyramine (NEN, Boston, Mass., USA) as peroxidase substrate, according to the suppliers' directions. LNCaP, PC-3, and DU-145 cells grown on slides were gently washed with phosphate-buffered saline (PBS) (10 mM sodium phosphate and 0.9% NaCl [pH 7.4]) prior to fixation. Cells and frozen tissue sections were fixed in freshly prepared 2% paraformaldehyde in PBS for 15 min at 4° C. After 3 washes in PBS for 10 min each, the endogenous peroxidase activity was blocked with 0.3% hydrogen peroxide in methanol for 30 min.

Following washes in distilled water for 5 min and in PBS for 20 min, cells and tissues were permeabilized with 0.2% Triton-X-100 (Sigma Chemical Co., St Louis, Mo., USA) and 1% normal goat (for HDAC1) serum (NGS) or 1% normal rabbit (for HDAC8) serum (NRS) (Vector Lab. Inc., Burlingame, Calif., USA) in PBS for 5 min on ice. The slides were then incubated 3 times with NGS or NRS 3% in PBS for 10 min to block the non specific serum-binding sites. Anti-HDAC1 Ab1 antiserum (Emiliani et al. (1998) supra) at a dilution of 1:200 or anti-HDAC8 Ab at a dilution of 1:200 was applied and incubated for 1 hr, followed by incubation with a biotinylated goat anti-rabbit (HDAC1) or rabbit anti-goat (HDAC8) Ig antibody and the avidin-biotin-peroxidase complex. After each incubation, the slides were washed 3 times with 1% NGS or NRS in PBS for 5 min. Peroxidase activity was developed for 8 min by a solution containing FITC-conjugated tyramine at a concentration of 1:50 in amplification diluent (MEN, Boston, Mass., USA). After 3 washes in PBS for 10 minutes, 4,6-diamidino-2-phenylindole (DAPI) 1:100 (15 min) was used to counterstain the slides, which were subsequently washed with PBS for 5 min and mounted with antifading fluorescent mounting medium (DAKO, Carpinteria, Calif., USA) for immunofluorescence microscopic examination. Photomicrographs of the slides were taken with a Leica DM microscope equipped with appropriate filter sets. Color photomicrographs were made from these slides under standard conditions to allow comparison in fluorescence intensities.

Immunofluorescence staining with the anti-HDAC1 antiserum was assessed in 5 representative prostate cancer tissue specimens and in their corresponding non neoplastic samples. Control experiments included omission of anti-HDAC1 or anti-HDAC8 antibody, use of the preimmune serum corresponding to Ab1 as first antibody, and preincubation of anti-HDAC1 or anti-HDAC8 antiserum with a 100 molar excess of the corresponding peptide prior to the antiserum's use in the immunostaining assay. Emiliani et al. (1998) *Proc. Natl. Acad. Sci. USA* 95:2795-2800.

HDAC1 and HDAC8 expression in normal and malignant prostate epithelial cells was also assessed using an immunoperoxidase technique. Immunoperoxidase was performed with the use of the ABC Vectastain Elite kit according to the supplier's directions with some modifications. Briefly, 5 μm formalin-fixed paraffin-embedded tissue sections were deparaffinized in xylene, rehydrated, and incubated with 0.25% Triton-X-100 in PBS for 10 min. After blocking of the endogenous peroxidase activity with 0.3% hydrogen peroxide in methanol for 30 min, the sections were incubated with a 10 mM citrate buffer (pH=6.0) at 95° C. for 40 min, allowed to cool down, and then incubated with 1% normal goat (HDAC1) or swine (HDAC8) serum in PBS for 30 min to block the nonspecific serum-binding sites. Anti-HDAC1 Ab1 at a dilution of 1:1000, anti-HDAC1 Ab2 at a dilution of 1:100, or anti-HDAC8 Ab at a dilution of 1:200 were applied and incubated overnight at 4° C., followed by biotinylated goat anti-rabbit (HDAC1) or swine anti-goat (HDAC8) Ig antibody and the avidin-biotin-peroxidase complex. Slides were washed three times with PBS after each incubation. Peroxidase activity was developed by a solution of 4 mg of 3-3' diaminobenzidine tetrahydrochloride (DAB) (Vel, Leuven, Belgium) dissolved in 10 ml of PBS and 0.03% $H_2O_2$. The DAB solution was filtered and applied to the sections for 4 minutes. Finally, Carazzi's hematoxylin was used to counterstain the slides that were then dehydrated and mounted. Immunoperoxidase staining was performed on 24 prostate cancer sections also containing non malignant prostate glands. These 24 samples were selected according to the Gleason score of the lesions (Gleason et al. (1974) *J. Urol.* 111:58-64): score 4 (grade 2+2, n=4), score 5 (grade 2+3, n=4), score 6 (grade 3+3, n=4), score 7 (grade 3+4, n=4), score 8 (grade 3+5, n=1; grade 4+4, n=3), and score 9 (grade 4+5, n=4).

Statistical Analysis

The Student t-test and the ANOVA test were used to assess whether pathologic stage and Gleason score, respectively, were significantly associated with tumor to normal HDAC1 mRNA and protein ratios. The ANOVA test was also used to determine whether tumor/normal HDAC protein ratios significantly correlated with tumor/normal HDAC mRNA or CK18 protein ratios. These statistical tests were two-tailed, and a p value <0.05 was considered statistically significant. The analyses were performed with the Statview II Version 4.2 software (Abacus Concepts Inc., CA, USA).

Results

Expression of Class I and Class II HDAC Transcripts in Human Prostate Cancer Cells Lines and Tissues Real time RT-PCR experiments were carried out to assess the relative abundance of HDAC1, HDAC2, HDAC3, HDAC4, HDAC5, HDAC6, HDAC7, and HDAC8 transcripts in total RNA extracts from DU-145, PC-3 and LNCaP human prostate cancer cells. The relative levels of HDAC1-8 transcripts in DU-145, PC-3, and LNCaP cells were arbitrarily compared to those obtained in LNCaP cells. As shown in FIG. 9A, all HDAC transcripts tested were detected in the 3 cell lines. Interestingly, the HDAC mRNA expression profiles of PC-3 and LNCaP cells were fairly similar with only slight variability, while the HDAC mRNA profile of DU-145 cells was more distinct. Indeed, HDAC3, HDAC4, HDAC5, and HDAC7 mRNA expression levels were at least twofold higher in these latter cells.

The relative levels of HDAC1-8 expression at the transcript level were next determined in total RNA extracts from human prostate cancer tissues and their corresponding normal counterpart. The relative abundance of each HDAC transcript in the tumor/normal sample pairs analyzed was calculated as a ratio between the HDAC transcript level in the tumor sample and the HDAC transcript level in the corresponding normal sample. The results obtained for HDAC8 mRNA are shown in FIG. 9B. In total, 16 tumor/normal prostate tissue pairs were screened for HDAC1 mRNA expression. The abundance of HDAC1 transcripts, normalized to the abundance of cyclophilin A mRNA, was equivalent in most of the matched prostate tumor and normal samples. Indeed, the HDAC1 mRNA ratios ranged between 0.75 and 1.25 in 12 of the 16 pairs tested (75%). Mean tumor/normal HDAC1 mRNA ratio for all sample pairs analyzed was 0.9±0.19 (median=0.83; range=0.64-1.41). Similar results were obtained when 18S rRNA was used as endogenous normalizer. Likewise HDAC1 transcript levels, the abundance of HDAC2 transcripts was similar in 9 matched prostate tumor and corresponding normal samples analyzed. The HDAC2 mRNA ratios ranged between 0.75 and 1.25 in 7 of the 9 pairs tested (77.8%). Mean tumor/normal HDAC2 mRNA ratio for all sample pairs analyzed was 0.83±0.14 (median=0.78; range=0.67-1.04). The tumor/normal HDAC3, HDAC4, HDAC5, HDAC6, HDAC7, and HDAC8 mRNA ratios were also assessed in the same 9 tissue sample pairs. As shown in FIG. 9B, the tumor/normal transcript ratios for these HDACs were distinctly more variable. Indeed, the tumor/normal transcript ratios for HDAC3, HDAC4, HDAC5, HDAC6, HDAC7, and HDAC8 were <0.5 in 2, 5, 4, 4, 4, and 4 of the 9 sample pairs analyzed, respectively. None of the tumor/normal mRNA ratios for these HDACs was >1.25.

FIGS. 9A and 9B. 9A) Analysis of HDAC1, HDAC2, HDAC3, HDAC4, HDAC5, HDAC6, HDAC7 and HDAC8 transcript levels by TaqMan® Real-Time RT-PCR in DU-145, PC-3 and LNCaP cells, as described in Materials and Methods. The specific human HDAC primers and probes used in the PCR reactions are shown in Table 5. The relative amounts of HDAC transcripts in each cell line were determined using the standard curve method and were normalized to cyclophilin A mRNA levels. Relative HDAC transcript level in each cell line was calculated as a ratio between the HDAC mRNA level in the cell line and the HDAC mRNA level in LNCaP cells. Samples were run in triplicates and error bars represent standard deviations. 9B) Prostate cancer and corresponding normal prostate tissues were harvested from radical prostatectomy specimens, as described in Materials and Methods. Total RNA was extracted from each tumor (T) and matched normal (N) sample. One µg of total RNA per sample was reverse-transcribed and one-tenth of each RT reaction was subjected to TaqMan® Real-Time PCR amplification. The relative amounts of HDAC transcripts in each sample were determined using the standard curve method and were normalized to cyclophilin A mRNA expression levels. Relative EDAC mRNA level in each tumor/normal sample pair was calculated as a ratio between HDAC mRNA level in the tumor sample and HDAC mRNA level in the corresponding normal sample. Error bars stand for standard deviation of the ratios.

The protein expression levels of HDAC1-8 were investigated by immunoblot, immunocytochemistry, and immunohistochemistry. For these experiments, various specific anti-HDAC antibodies were used. Specific signals/stainings were obtained for HDAC1, HDAC5, and HDAC8 enzymes.

Expression of HDAC1 Protein in Human Prostate Cancer Cell Lines and Tissues

Immunoblotting performed on total protein extracts from DU-145, PC-3 and LNCaP cells showed the presence of an expected 60 E) band corresponding to HDAC1 (FIG. 10). Higher levels of HDAC1 were detected in LNCaP cells than in DU-145 and PC-3 cells. Similar patterns of HDAC1 abundance in the 3 cell lines were obtained with the 3 different anti-HDAC1 antibodies used.

Immunocytofluorescence experiments, with the use of anti-HDAC1 Ab1, showed that the enzyme was exclusively detected in the nucleus of all DU-145, PC-3 and LNCaP cells grown on glass slides. Control experiments in which the anti-HDAC1 antiserum was preincubated with a molar excess of the corresponding peptide completely abolished the labeling. Similarly, no specific staining was observed when the preimmune serum was used or when the primary antibody was replaced with PBS in the immunofluorescence procedure.

FIG. 10. Protein lysates (30 µg per lane) from human DU-145, PC-3, and LNCaP prostate cancer cells were subjected to immunoblot analysis of HDAC1 expression, as described in Materials and Methods.

To search for HDAC1 expression in human prostate cancer tissues, we first performed immunoblots on total protein extracts prepared from prostate tissue cylinders obtained as described in 'Materials and Methods'. HDAC1 expression in prostate cancer specimens and corresponding normal tissue samples from 20 radical prostatectomies was evaluated. The pathological stage and the Gleason score of the lesions analyzed are detailed in Table 6.

Table 6 Pathological Characteristics of 24 Prostate Cancer Samples Obtained from Radical Prostatectomy Specimens

TABLE 2

Pathologic characteristics of 24 prostate cancer samples obtained from radical prostatectomy specimens.

| Sample | Gleason score | Pathologic stage |
|---|---|---|
| T1 | 6 | pT2B |
| T2 | 6 | pT3A |
| T3 | 6 | pT3B |
| T4 | 6 | pT2B |
| T5 | 8 | pT3A |
| T6 | 7 | pT2B |
| T7 | 6 | pT3B |
| T8 | 7 | pT2B |
| T9 | 5 | pT3A |
| T10 | 6 | pT3B |
| T11 | 6 | pT3A |
| T12 | 6 | pT3A |
| T13 | 6 | pT3A |
| T14 | 6 | pT2B |
| T15 | 7 | pT2B |
| T16 | 5 | pT3A |
| T17 | 6 | pT2B |
| T18 | 6 | pT3A |
| T19 | 6 | pT3A |
| T20 | 6 | pT3B |
| T21 | 7 | pT3A |
| T22 | 6 | pT2B |
| T23 | 7 | pT3A |
| T24 | 6 | pT2B |

Immunoblotting experiments were carried out first with the use of 5 different tumor/normal pairs and either Ab1 or Ab3; similar patterns of HDAC1 expression were observed. A 60 kD band corresponding to HDAC1 was obtained in all 20 tissue samples tested. The abundance of HDAC1 in the matched malignant and non malignant prostate specimens from each patient was determined. In 15 out of the 20 cases tested (75%), prostate cancer lesions were found to express higher amounts of the enzyme than the corresponding non-malignant counterpart. Mean tumor/normal HDAC1 ratio for the entire set of tissue pairs was 1.63±1.12 (median=1.25; range=0.61-4.23). In 5 sample pairs, HDAC1 tumor/normal ratio was ≧2. No significant association was found between tumor/normal HDAC1 protein ratio and either the pathologic stage (Student t-test, p=0.64) or the Gleason score of the lesions (ANOVA test, p=0.58).

Because of the well-known heterogeneity of prostate cancer lesions and since it is virtually impossible to obtain 100% pure prostate cancer tissues (not contaminated with non malignant glands), the expression of HDAC1 protein at the cellular level was examined using immunofluorescence staining performed on frozen tissue sections bearing prostate cancer. In order to compare the level of nuclear HDAC1 expression in all the cells present in the samples, the nuclei were counterstained with DAPI. HDAC1 expression was found to be exclusively expressed in the nucleus of non-malignant and malignant epithelial cells. In all 5 samples examined, nuclear fluorescence intensity appeared to be equivalent in cancer cells and in non-malignant epithelial cells.

The analysis of HDAC1 protein expression was extended to a series of paraffin-embedded prostate cancer lesions with various levels of differentiation using an immunoperoxidase technique. Sections from 24 prostate tissues containing both malignant and non-malignant prostate epithelial cells were immunostained with anti-HDAC1 Ab2 antibody. Anti-HDAC1 immunoreactivity was detected in the nucleus of all normal and malignant epithelial cells and no difference in staining intensity was observed between normal and cancerous epithelial cells. The intensity of anti-HDAC1 nuclear reactivity in the tumor cells was not altered by the level of differentiation of the cancer lesions, expressed as the Gleason score. Similar results were obtained with the use of anti-HDAC1 Ab1 antibody.

Anti-HDAC1 labeling was detected in both basal and secretory epithelial cells from normal prostate glands, as well as in endothelial and inflammatory cells. Both immunofluorescence and immunoperoxidase experiments showed that most prostate stromal cells usually exhibited a low or no detectable level of nuclear HDAC1 expression.

Since HDAC1 nuclear abundance was higher in epithelial than in stromal cells, we hypothesized that the increased expression of HDAC1 in tumor samples, as determined by immunoblot, was the result of an increased proportion of epithelial cells in the malignant samples as compared with their normal counterpart. Immunoblot experiments using an antibody directed against cytokeratin 18 (CK18), a specific epithelial marker, showed that CK18 expression levels were usually higher in the tumor samples than in the matched normal samples. Mean T/N CK18 ratio was 1.58±0.71 (median=1.33; range=0.87-3.82). Tumor/normal CK18 ratios closely paralleled tumor/normal HDAC1 ratios (ANOVA test, p=0.004).

Expression of HDAC8 Protein in Human Prostate Cancer Cell Lines and Tissues

A unique band at ±45 kD was observed in the 3 prostate cancer cells lines tested for HDAC8 expression by immunoblot (FIG. 11A). The abundance of HDAC8 protein was higher in DU-145 and PC-3 cells than in LNCaP cells. Immunoblot analysis of HDAC8 expression levels in the human prostate tissues revealed that the abundance of the enzyme was usually lower in the cancer samples than in the corresponding normal ones (FIG. 11B). Mean T/N HDAC8 protein ratio for all 13 sample pairs analyzed was 0.76±0.14 (median=0.75; range=0.52-1.01). HDAC8 transcript levels were also decreased in most tumor samples as compared with the matching normal samples, with a mean T/N HDAC8 mRNA ratio of 0.63±0.26 (median=0.60; range=0.29-1.02). T/N HDAC8 protein ratios were significantly correlated with T/N HDAC8 mRNA ratios (ANOVA test; p=0.035).

FIGS. 11A and 11B. 11A) Protein lysates (30 µg per lane) from human DU-145, PC-3, and LNCaP prostate cancer cells were subjected to immunoblot analysis of HDAC8 expression, as described in Materials and Methods. 11B) Prostate cancer and corresponding normal prostate tissues were harvested from radical prostatectomy specimens, as described in Materials and Methods. Total proteins were isolated from each tumor (T) and matched (N) normal sample. Protein lysates (30 kg per sample) were subjected to Western blot analysis of HDAC8.

The expression of HDAC8 protein at the cellular level was examined using immunofluorescence staining performed on frozen prostate tissue sections. HDAC8 expression was found to be mainly expressed in the cytoplasm of stromal prostate cells. In all 5 samples examined, no anti-HDAC8 immunostaining was detected in normal or malignant epithelial prostate cells.

HDAC8 protein expression was further analyzed by immunoperoxidase staining in the series of 24 paraffin-embedded prostate tissues bearing cancer lesions with various levels of differentiation, Pre-incubation of the anti-HDAC8 antibody with the corresponding peptide completely abolished the immunostaining. Anti-HDAC8 immunoreactivity was not detected in the normal or malignant epithelial cells in any of the cases analyzed. HDAC8 protein was expressed by most stromal cells either adjacent to normal glands or intermingled with cancer glands or cells.

Expression of HDAC5 Protein in Human Prostate Cancer Cell Lines and Tissues.

A unique band at ±165 kD was observed in all 3 prostate cancer cells lines tested for HDAC5 expression by immunoblot. The pattern of HDAC5 protein expression in these cells was similar to that of HDAC8 expression, with amounts of HDAC5 protein in DU-145>PC-3>LNCaP cells. No HDAC5 expression was detected in any of the normal or malignant prostate tissues tested by immunoblot, even after prolonged exposure of the membranes.

The relative abundance of HDAC1 and HDAC8 transcripts was compared in the non-malignant prostate tissues using real-time RT-PCR. The mean threshold cycle ($C_T$) for HDAC5 amplification was substantially higher than the mean $C_T$ for HDAC1 (24.5 versus 19.8, respectively, when 100 ng of RNA were used as template). Thus, it could be estimated that HDAC5 transcripts were 20 times less abundant than HDAC 1 transcripts in these tissues.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disorder associated with smooth muscle cell hyperactivity, the method comprising administering to an individual in need thereof an effective amount of an agent that reduces histone deacetylase-8 (HDAC8) enzyme activity and/or an HDAC8 mRNA expression level in a smooth muscle cell.

2. The method of claim 1, wherein the disorder is selected from hypertension, asthma, atherosclerosis, myometrium hyperactivity, bladder overactivity, benign hyperplasia of the prostate, fibrosis, and hypertrophic scars.

3. The method of claim 1, wherein the agent is a short interfering RNA (siRNA) specific for HDAC8 mRNA or a nucleic acid comprising a nucleotide sequence encoding an siRNA specific for HDAC8 mRNA.

4. The method of claim 3, wherein the siRNA comprises nucleotide sequences that are complementary to a nucleotide sequence of at least 19 nucleotides present in the HDAC8 mRNA.

5. The method of claim 1, wherein the agent is a nucleic acid comprising a nucleotide sequence encoding a short interfering RNA (siRNA) specific for HDAC8 mRNA.

6. The method of claim 5, wherein the siRNA-encoding nucleotide sequence is operably linked to a promoter that is functional in a smooth muscle cell.

7. The method of claim 4, wherein the siRNA comprises the nucleotide sequences set forth in SEQ ID NO:8 and SEQ ID NO:9.

8. The method of claim 4, wherein the siRNA comprises the nucleotide sequences set forth in SEQ ID NO:10 and SEQ ID NO:11.

9. The method of claim 5, wherein the si-RNA-encoding nucleic acid comprises the nucleotide sequence 5'-TGAGC-CCCACCGAATCCAA(X)$_n$TTGGATTCG-GTGGGGCTCA-3' (SEQ ID NO:12), wherein X is any nucleotide and wherein n is an integer from 1 to 10.

10. The method of claim 9, wherein the si-RNA-encoding nucleic acid comprises the nucleotide sequence set forth in SEQ ID NO:13.

11. The method of claim 5, wherein the si-RNA-encoding nucleic acid comprises the nucleotide sequence 5'-ACGGGCCAGTATGGTGCAT(X)$_n$ATGCACCAT-ACTGGCCCGT-3' (SEQ ID NO:14), wherein X is any nucleotide and wherein n is an integer from 1 to 10.

12. The method of claim 11, wherein the si-RNA-encoding nucleic acid comprises the nucleotide sequence set forth in SEQ ID NO:15.

13. The method of claim 1, wherein the agent specifically reduces the level of active HDAC8 in a smooth muscle cell selected from a visceral smooth muscle cell, a vascular smooth muscle cell, a myoepithelial cell, and a myofibroblast.

* * * * *